(12) United States Patent
Abbasi

(10) Patent No.: US 11,058,551 B2
(45) Date of Patent: Jul. 13, 2021

(54) INTERBODY IMPLANT WITH CONCAVE PROFILED NOSE

(71) Applicant: ADVANCE RESEARCH SYSTEM, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 72 days.

(21) Appl. No.: 16/469,569

(22) PCT Filed: Dec. 15, 2017

(86) PCT No.: PCT/US2017/066641
§ 371 (c)(1),
(2) Date: Jun. 13, 2019

(87) PCT Pub. No.: WO2018/112324
PCT Pub. Date: Jun. 21, 2018

(65) Prior Publication Data
US 2020/0138589 A1    May 7, 2020

Related U.S. Application Data

(60) Provisional application No. 62/435,598, filed on Dec. 16, 2016, provisional application No. 62/524,079, filed on Jun. 23, 2017.

(51) Int. Cl.
*A61F 2/44* (2006.01)
*A61F 2/46* (2006.01)
*A61F 2/30* (2006.01)

(52) U.S. Cl.
CPC .............. *A61F 2/446* (2013.01); *A61F 2/447* (2013.01); *A61F 2/4611* (2013.01);
(Continued)

(58) Field of Classification Search
CPC ........ A61F 2/446; A61F 2/447; A61F 2/4611; A61F 2002/30113; A61F 2002/30116;
(Continued)

(56) References Cited

U.S. PATENT DOCUMENTS

| | | | |
|---|---|---|---|
| 6,443,987 | B1 | 9/2002 | Bryan |
| 6,942,698 | B1 | 9/2005 | Jackson |

(Continued)

FOREIGN PATENT DOCUMENTS

| | | |
|---|---|---|
| EP | 1099429 A1 | 5/2001 |
| FR | 2946245 | 12/2010 |

(Continued)

OTHER PUBLICATIONS

Design World "Peek thermoplastic used to develop spinal spacer devices" (Nov. 29, 2012) downloaded from internet at http://www.designworldonline.com/peek-thermoplastic-used-to-develop-spinal-spacer-devices/.

(Continued)

*Primary Examiner* — Pedro Philogene
(74) *Attorney, Agent, or Firm* — Christensen, Fonder, Dardi & Herbert PLLC

(57) ABSTRACT

An interbody implant and inserter tool for spinal fusion. The interbody implant includes a cage portion and a nose portion. In some embodiments, an outer surface of the nose portion defines at least a first concave profile in a first direction, and may define a second concave profile in a second direction, the second direction being perpendicular to the first direction. The outer surface may also define an oblong cross-section normal to a nose axis. The oblong cross-section may be axisymmetric or continuously curved (or both) about the nose axis. The concave profile(s) enable easier initial insertion of for more precisely locating the interbody implant, so that the greater insertion forces (Continued)

required during implantation do not occur until the interbody implant is securely and accurately placed.

20 Claims, 17 Drawing Sheets

(52) U.S. Cl.
CPC .............. *A61F 2002/30113* (2013.01); *A61F 2002/30116* (2013.01); *A61F 2002/30125* (2013.01); *A61F 2002/30593* (2013.01); *A61F 2002/30904* (2013.01); *A61F 2002/4627* (2013.01); *A61F 2002/4629* (2013.01); *A61F 2310/00023* (2013.01)

(58) Field of Classification Search
CPC .. A61F 2002/30125; A61F 2002/30593; A61F 2002/30904; A61F 2002/4627; A61F 2002/4629; A61F 2310/00023
See application file for complete search history.

(56) References Cited

U.S. PATENT DOCUMENTS

| | | |
|---|---|---|
| 7,105,023 B2 | 9/2006 | Eckman |
| 7,175,667 B2 | 2/2007 | Saunders et al. |
| D552,734 S | 10/2007 | Eckman |
| 7,534,267 B2 | 5/2009 | Eckman |
| 7,674,295 B2 | 3/2010 | Eckman |
| D619,719 S | 7/2010 | Pannu |
| D620,110 S | 7/2010 | Courtney et al. |
| D620,112 S | 7/2010 | Courtney et al. |
| D620,113 S | 7/2010 | Courtney et al. |
| D627,468 S | 11/2010 | Richter et al. |
| 7,850,734 B2 | 12/2010 | Oh et al. |
| D630,749 S | 1/2011 | Tornier |
| 7,867,277 B1 | 1/2011 | Tohmeh |
| 7,938,857 B2 | 5/2011 | Garcia-Bengochea et al. |
| 8,002,831 B2 | 8/2011 | Burd et al. |
| 8,025,697 B2 | 9/2011 | McClellan, III et al. |
| 8,062,374 B2 | 11/2011 | Markworth et al. |
| D653,757 S | 2/2012 | Binder |
| 8,137,402 B2 | 3/2012 | Eckman |
| 8,147,554 B2 | 4/2012 | Hansell et al. |
| 8,167,886 B2 | 5/2012 | Eckman |
| D665,081 S | 8/2012 | Hansell et al. |
| 8,273,128 B2 | 9/2012 | Oh et al. |
| D675,736 S | 2/2013 | Garza-Vale et al. |
| 8,414,654 B1 | 4/2013 | Ganey |
| 8,425,610 B2 | 4/2013 | Guyer et al. |
| 8,496,709 B2 * | 7/2013 | Schell ................... A61F 2/4455 623/17.16 |
| 8,535,378 B2 | 9/2013 | Jackson |
| 8,568,416 B2 | 10/2013 | Schmitz et al. |
| 8,591,589 B2 | 11/2013 | McCombe et al. |
| 8,613,745 B2 | 12/2013 | Bleich |
| 8,617,163 B2 | 12/2013 | Bleich |
| 8,663,331 B2 | 3/2014 | McClellan, III et al. |
| 8,679,189 B1 | 3/2014 | Ganey et al. |
| 8,685,096 B2 | 4/2014 | Davenport |
| 8,709,087 B2 | 4/2014 | Cragg |
| 8,747,473 B2 | 6/2014 | Burd et al. |
| 8,845,727 B2 | 9/2014 | Gottlieb et al. |
| 8,864,839 B2 | 10/2014 | Ganey |
| 8,870,957 B2 | 10/2014 | Vraney et al. |
| D718,860 S | 12/2014 | Farris et al. |
| 8,900,310 B2 | 12/2014 | Carlson et al. |
| D722,695 S | 2/2015 | Kaufmann et al. |
| 8,979,927 B2 | 3/2015 | Huntsman et al. |
| 8,992,622 B2 | 3/2015 | Ullrich, Jr. et al. |
| 9,015,922 B2 | 4/2015 | Ganey |
| D731,063 S | 6/2015 | VerHage et al. |
| D732,667 S | 6/2015 | McCormack et al. |
| D733,303 S | 6/2015 | Peterson et al. |
| D737,446 S | 8/2015 | Butler et al. |
| 9,107,768 B2 | 8/2015 | Schell et al. |
| 9,138,330 B2 | 9/2015 | Hansell et al. |
| D741,488 S | 10/2015 | Tohmeh et al. |
| D745,156 S | 12/2015 | McCormack et al. |
| 9,198,774 B2 | 12/2015 | Pisharodi |
| 9,226,835 B2 | 1/2016 | Schell et al. |
| D750,249 S | 2/2016 | Grimberg, Jr. et al. |
| 9,265,622 B2 | 2/2016 | Schell et al. |
| 9,289,312 B2 | 3/2016 | Davenport et al. |
| 9,295,562 B2 | 3/2016 | Lechmann et al. |
| D753,305 S | 4/2016 | Butler |
| 9,320,610 B2 | 4/2016 | Alheidt et al. |
| 9,320,618 B2 | 4/2016 | Schmitz et al. |
| 9,364,344 B2 | 6/2016 | Whipple |
| 9,381,049 B2 | 7/2016 | McCormack et al. |
| 9,445,914 B2 | 9/2016 | Milz et al. |
| 9,566,170 B2 | 2/2017 | Schell et al. |
| 2002/0169508 A1 | 11/2002 | Songer et al. |
| 2003/0023306 A1 | 1/2003 | Liu et al. |
| 2003/0105528 A1 | 6/2003 | Shimp et al. |
| 2003/0139812 A1 | 7/2003 | Garcia et al. |
| 2006/0167548 A1 | 7/2006 | Jackson |
| 2009/0138015 A1 * | 5/2009 | Conner ............. A61B 17/1671 606/80 |
| 2011/0144755 A1 | 6/2011 | Baynham et al. |
| 2012/0065613 A1 | 3/2012 | Pepper et al. |
| 2014/0100657 A1 | 4/2014 | McCormack et al. |
| 2015/0005881 A1 | 1/2015 | Connor et al. |
| 2015/0100129 A1 | 4/2015 | Waugh et al. |
| 2015/0173917 A1 * | 6/2015 | Radcliffe ............... A61F 2/4455 623/17.16 |
| 2016/0030188 A1 | 2/2016 | Lynn et al. |
| 2016/0081814 A1 | 3/2016 | Baynham |
| 2016/0113773 A1 | 4/2016 | Ganem |
| 2018/0243097 A1 * | 8/2018 | Jones .................... B33Y 80/00 |

FOREIGN PATENT DOCUMENTS

| | | |
|---|---|---|
| KR | 30-0543254 | 4/2010 |
| WO | WO2013/009462 A2 | 1/2013 |

OTHER PUBLICATIONS

Nexxt Spine "Honour tPLIF Spacer System" downloaded from the internet at http://nexxtspine.com/products/honour-tplif-spacer-system, published prior to Feb. 13, 2017.
Notice of Allowance received for Japanese Design Application No. 2017-28954, dated Apr. 20, 2018.
Next Spine "Honour tPLIF Spacer System" downloaded from the internet on Oct. 20, 2017 at http://www.nexxtspine.com/gallery/honour_tplif/new/169.
Next Spine "Honour TLIF Spacer System" downloaded from the internet on Oct. 20, 2017 at http://www.nexxtspine.com/products/Honour-TLIF-Spacer-System.
Next Spine "Honour Allo-C Allograft System" downloaded from the internet on Oct. 20, 2017 at http://www.nexxtspine.com/products/honour-allo-c-allgraft-system.
International Search Report for Application No. PCT/US2017/066641 dated Jun. 25, 2018 (6 pages).
Next Spine "Honour Orb Cervical Spacer System" downloaded from the internet on Oct. 20, 2017 at http://www.nexxtspine.com/products/honour-orb-cervical-spacer-system.

* cited by examiner

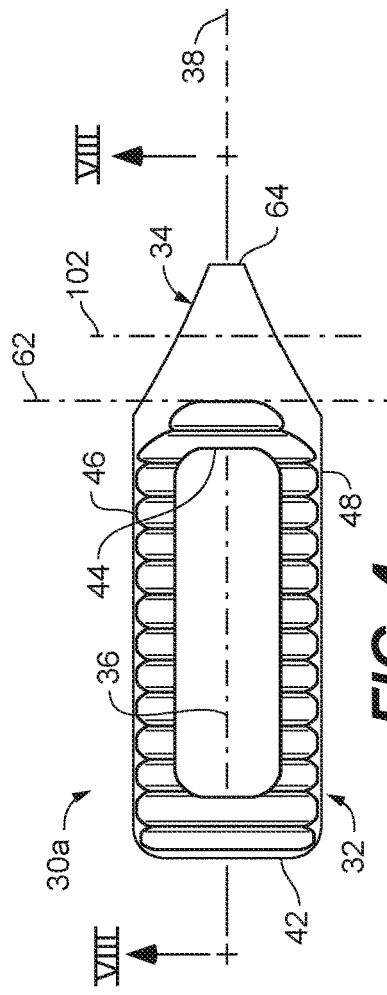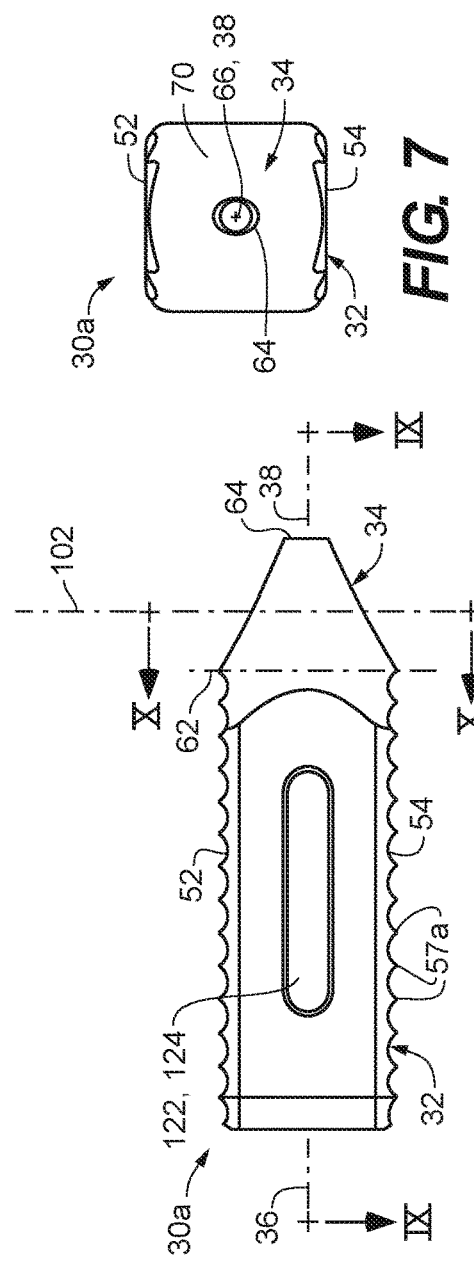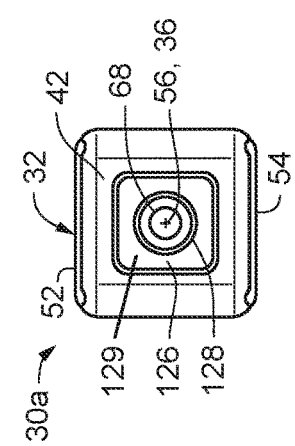
FIG. 4
FIG. 5
FIG. 6
FIG. 7

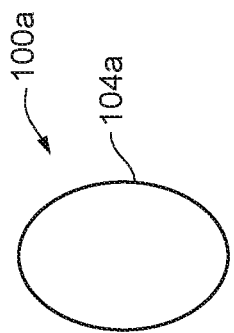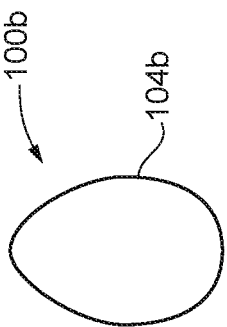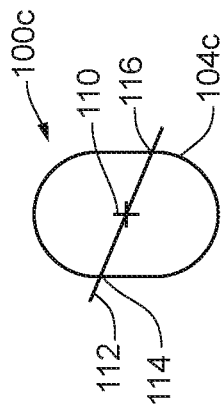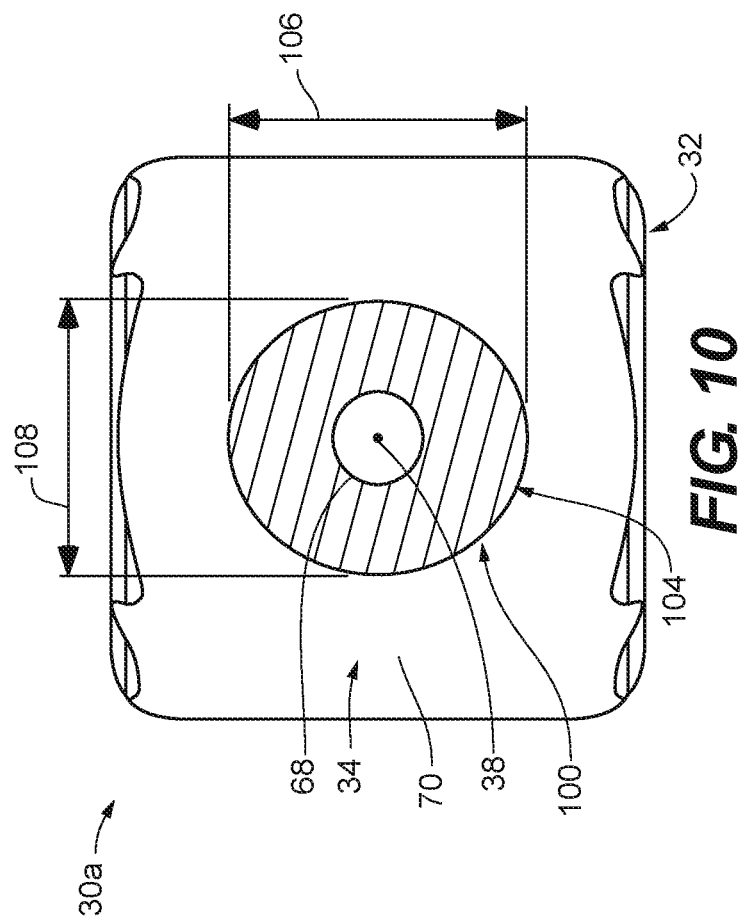

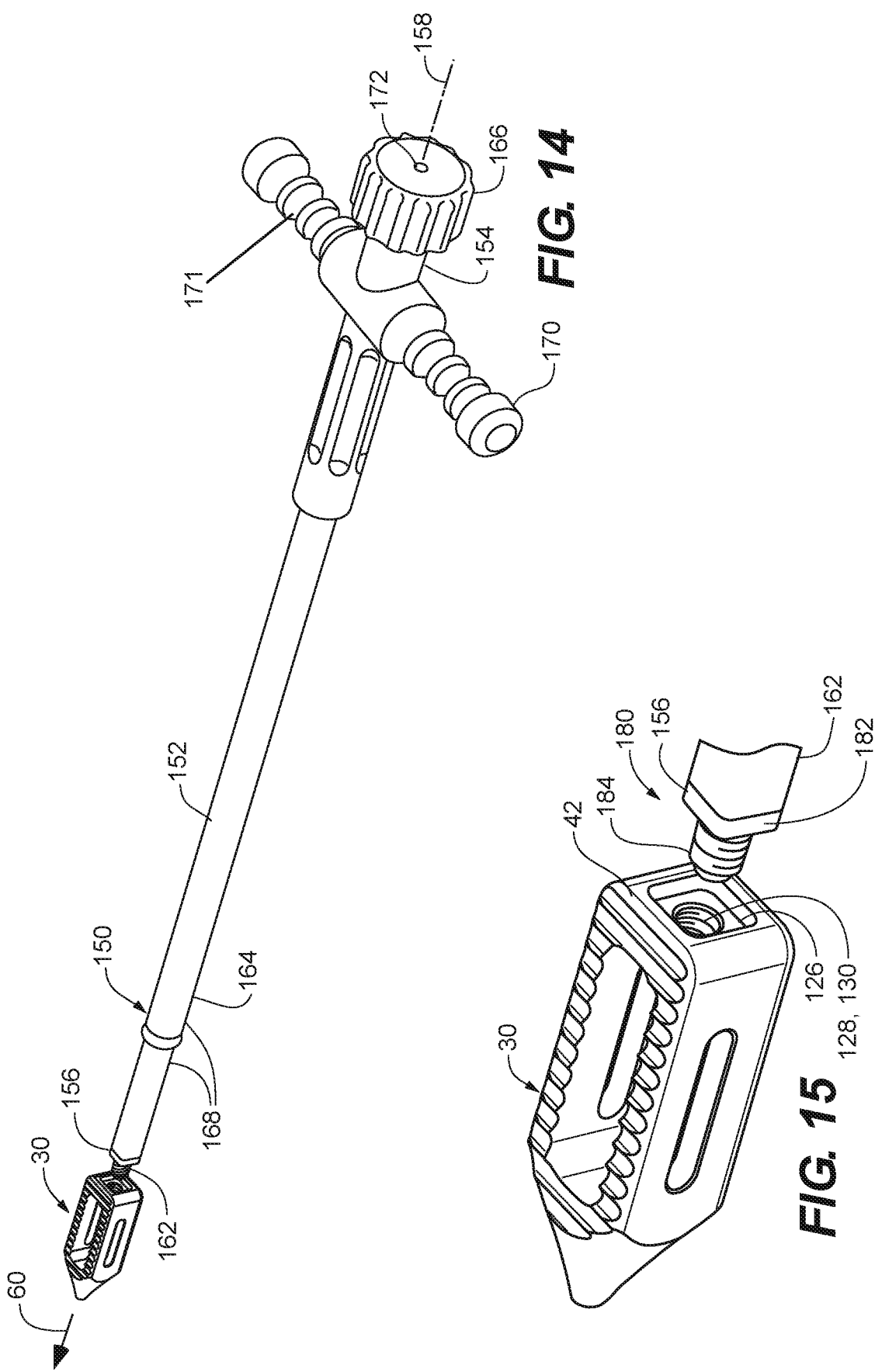

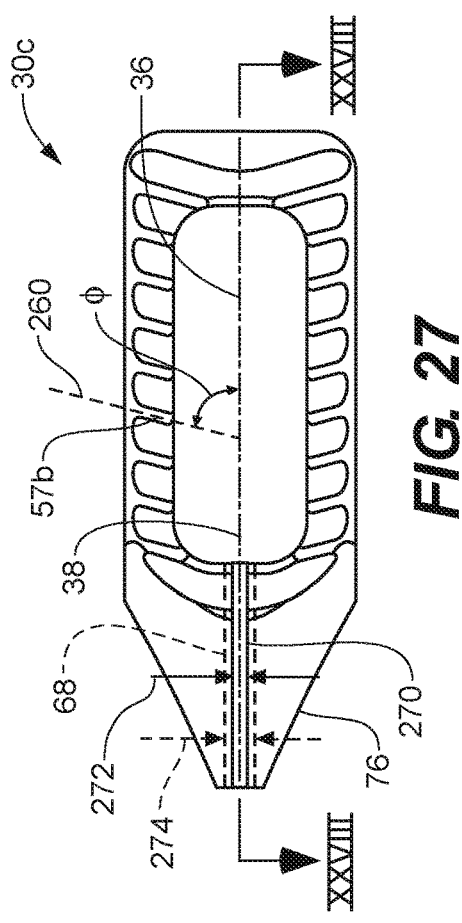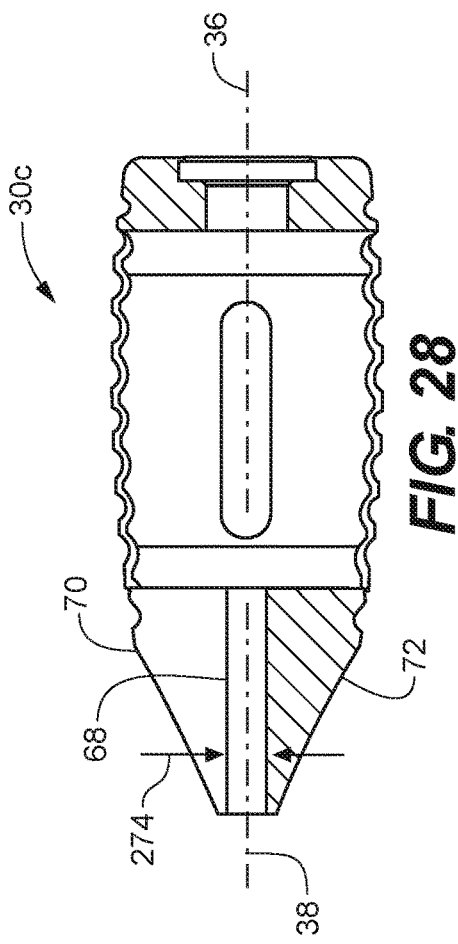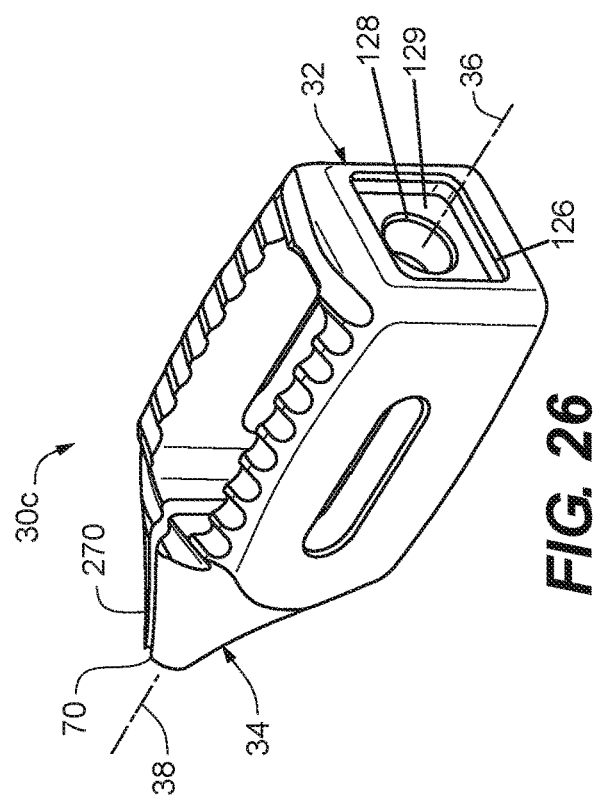

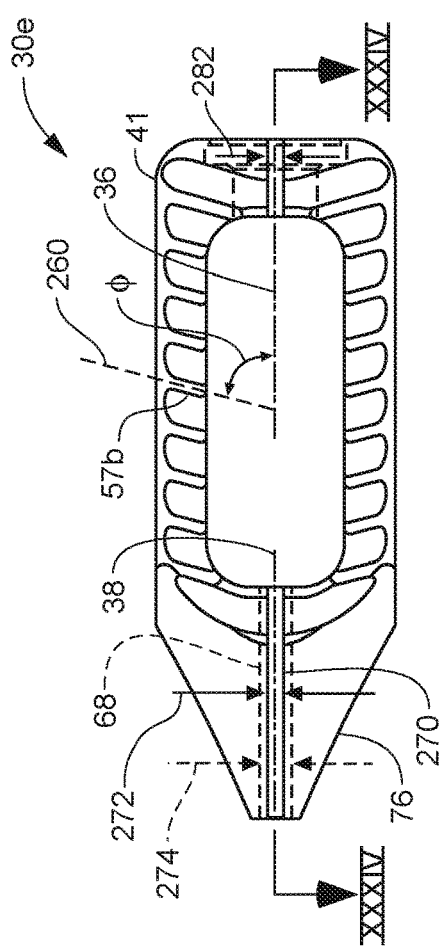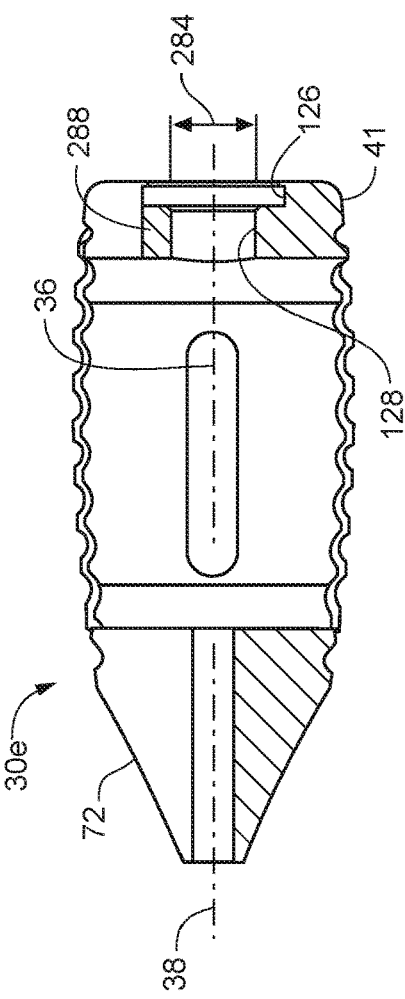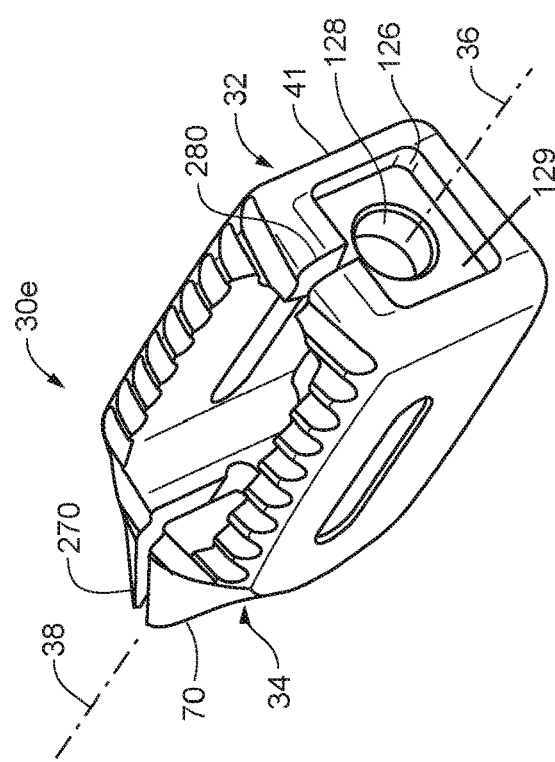

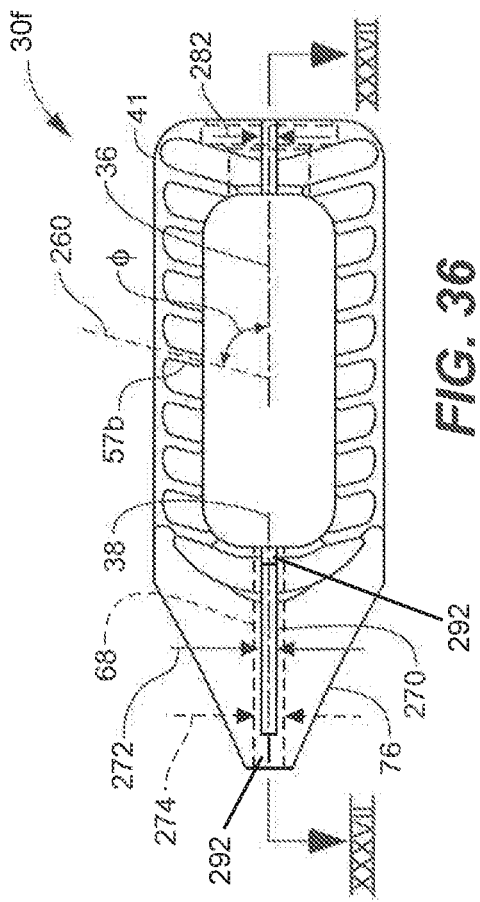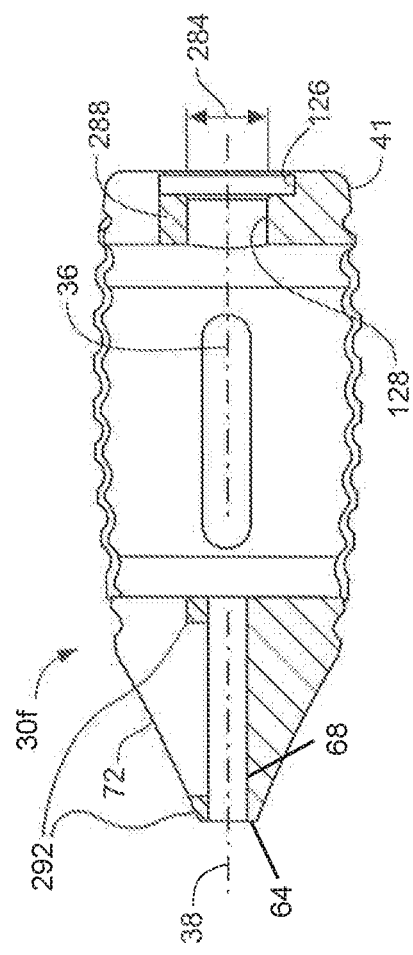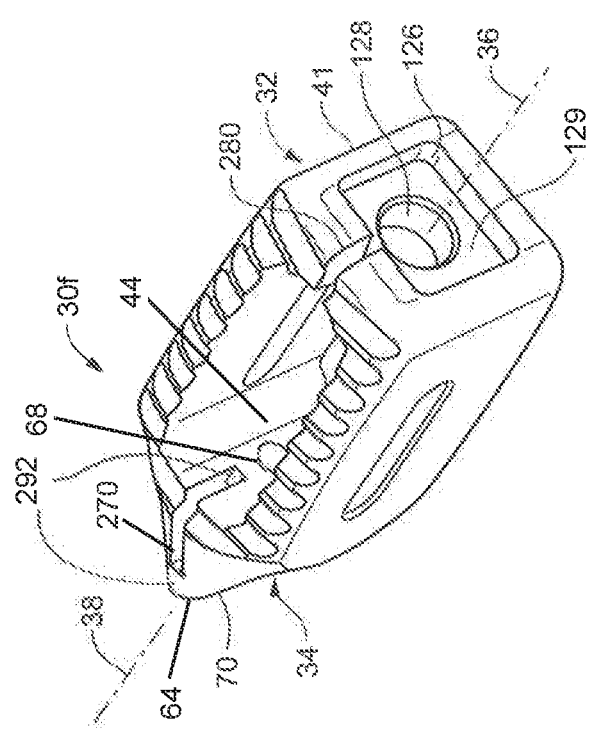

INTERBODY IMPLANT WITH CONCAVE PROFILED NOSE

RELATED APPLICATIONS

The present application is a National Phase entry of PCT Application No. PCT/US2017/066641, filed Dec. 15, 2017, which claims the benefit of U.S. Provisional Patent Application No. 62/435,598, filed Dec. 16, 2016, and of U.S. Provisional Patent Application No. 62/524,079, filed Jun. 23, 2017, the disclosures of which are hereby incorporated by reference herein in their entirety.

FIELD OF THE DISCLOSURE

The disclosure relates generally to interbody implants for spinal fusion, and more specifically to spinal cage implants having insertion tips.

BACKGROUND OF THE DISCLOSURE

Interbody implants are utilized for spinal fusion (arthrodesis) to restrict movement between vertebrae. The implants support and immobilize adjacent vertebrae while new bone tissue grow between the vertebrae.

Surgically implanting the interbody implants requires placement of the implant at desired locations and orientations, and in some procedures require substantial manipulation forces (thrust and torque) to accomplish insertion of the implant. Many interbody implants include a cage through which the new bone tissue can grow with a nose portion that aids in the insertion. However, forces associated with the implantation of these interbody implants can be prohibitive, resulting in high stresses on the vertebrae during implantation.

An interbody implant and implant system that facilitates implantation of the cage while reducing the manipulation forces associated with implantation would be welcomed.

SUMMARY OF THE DISCLOSURE

Various embodiments of the disclosed cage-type interbody implant facilitates insertion of the implant at reduced forces relative to conventional cage-type interbody implants. The profile of a nose portion of the interbody implant provides a small cross-sectional area proximate the distal end of the nose portion that is readily inserted into gaps within the spine structure. The outer surface of the nose portion slopes more gradually at the distal locations of the nose portion than at the proximal or base portions of the nose. This enables the nose portion to become firmly yet easily aligned within the desired entry location between adjacent vertebrae before the maximum manipulation forces are applied for final insertion.

In some embodiments, the outer surface nose portion defines a cross-section perpendicular to a nose axis, the cross-sections defining rounded surfaces that substantially reduce or eliminate adjacent flats or straight portions and associated transition corners therebetween. Such flats and transition corners are common in conventional interbody implants, and can inhibit rotational manipulation of the implant during insertion. The rounded surfaces enable easier rotation and reduce the torsional manipulation forces of the interbody implant. The ease of rotation and reduced torsional manipulation forces are particularly notable during initial alignment and insertion of the nose portion, where only the distal portion of the nose having a small insertion cross-section is engaged with the targeted vertebrae.

In some embodiments, an implant system facilitates guidance of the interbody implant to the desired location in the spine and at a desired orientation. An inserter is configured for rotational and thrust manipulation, and may include a guide wire. The interbody implant may be configured to accommodate the guide wire, so that the implant system more accurately guides the interbody implant to the target location.

Structurally, various embodiments of the disclosure include an interbody implant comprising a cage portion defining a cage axis that passes through a proximal portion and a distal portion thereof, and a nose portion extending in a distal direction from the distal portion of the cage portion, the nose portion defining a nose axis that is concentric with the cage axis, the nose axis extending in the distal direction from the cage portion through a distal extremity of the nose portion, the nose portion defining an outer surface about the nose axis that tapers toward the nose axis in the distal direction. The nose axis may be linear. In some embodiments, the interbody implant is titanium.

In some embodiments, the outer surface defines a first concave profile in a first direction from the nose axis, the first direction being perpendicular to the nose axis. In some embodiments, the nose portion defines a through-passage concentric about the nose axis, wherein: the cage portion and the nose portion define a through-passage concentric about the nose axis and the cage axis, the through-passage defining a minimum diameter, and at least one of the cage portion and the nose portion defines a first slot that extends from the through-passage through an exterior surface of the interbody implant, the first slot being in fluid communication with the through-passage, the first slot being coplanar with at least one of the nose axis and the cage axis and defining a gap dimension that is less than the minimum diameter of the through-passage.

In some embodiments, the first concave profile and the nose axis are co-planar. The second concave profile and the nose axis may also be co-planar. In some embodiments, the first concave profile is different from the second concave profile. Also, the first concave profile may define a first concavity and the second concave profile a second concavity, the first concavity being greater than or less than the second concavity.

In some embodiments, a second slot extends through an outer surface of the proximal portion of the cage portion, the second slot being coplanar with the cage axis. The first slot and the second slot may be coplanar. In some embodiments, a rib bridges the first slot proximate the through passage. The rib may be disposed at one of the distal portion of the cage portion and the distal extremity of the nose portion.

In some embodiments, the outer surface of the nose portion defines a second concave profile in a second direction from the nose axis, the second direction being perpendicular to the first direction at any point along the nose axis. The outer surface of the nose portion may define an oblong cross-section at a cross-section plane that intersects and is orthogonal to the nose axis, the oblong cross section defining a major dimension and a minor dimension, the minor dimension being perpendicular to the major dimension. In some embodiments, the oblong cross-section is continuously curved. In one example, the oblong cross-section is elliptical. A ratio of the major dimension to the minor dimension is in a range of: 1.05 to 1.20 inclusive;

1.05 to 1.15 inclusive;
1.07 to 1.12 inclusive. In some embodiments, the cross-section plane intersects the nose axis at a midpoint that is equidistant between the base plane and the distal extremity.

In some embodiments of the disclosure, the proximal portion of the cage portion includes a proximal wall and the distal portion of the cage portion includes a distal wall. The proximal wall and the distal wall are separated by opposing side walls. The proximal wall, distal wall, and opposing side walls define a superior edge surface and an inferior edge surface. The cage axis may pass through a center of the proximal wall and a center of the distal wall. In some embodiments, at least one of the superior edge surface and the inferior edge surface defines a plurality of gripping facets. Each of the plurality of gripping facets may define a ridge that extends along a ridge line, the ridge line extending proximally at a swept angle relative to the cage axis, the swept angle defining an acute angle. Each of the opposing side walls defines a side graft window that passes therethrough. In some embodiments, the side graft window defines an elongate slot. The elongate slot may extend substantially parallel to the cage axis. In some embodiments, the proximal wall defines an exterior recess and a through-hole, the through-hole being defined at a distal face of the exterior recess and concentric about the cage axis. The exterior recess may be polygonal.

In some embodiments, the nose portion and distal wall define a through-passage concentric about the nose axis, the nose axis being concentric with the cage axis. At least one of the superior edge surface and the inferior edge surface defines a convex profile that is arcuate about a lateral axis, the lateral axis being perpendicular to the cage axis and passing through the opposing side walls. In some embodiments, the nose portion extends from a base plane proximate the distal portion of the cage portion, the base plane being orthogonal to the nose axis. The outer surface of the nose portion may be axisymmetric about the nose axis.

In various embodiments of the disclosure, an interbody implant for treatment of a spine comprises an interbody implant including a nose portion defining a nose axis and having a distal extremity and a mid portion. The distal extremity defines a first cross-section that is orthogonal to the nose axis, the nose portion including an outer surface that is axisymmetric about the nose axis, the outer surface defining a first slope at the distal extremity that is coplanar with the nose axis, the first slope defining a first acute angle relative to the nose axis. The mid portion defines a second cross-section that is orthogonal to the nose axis, the outer surface defining a second slope at the mid portion that is coplanar with the first slope, the second slope defining a second acute angle relative to the nose axis. The first cross-section is smaller than the second cross-section, and the first acute angle is smaller than the second acute angle. In some embodiments, each of the first cross-section and the second cross-section defines a shape that is one of a circular shape and an oblong shape.

In various embodiments of the disclosure, a method for implanting an interbody implant is disclosed, comprising providing a kit including the interbody implant and a set of instructions on a tangible, non-transitory medium for implanting the interbody implant, the instructions including: guiding the interbody implant for implantation at a target location; inserting the distal extremity of the nose portion of the interbody implant for implantation into the target location; and initially thrusting the mid portion of the nose portion for penetration of the target location, wherein the first cross-section being smaller than the second cross-section, the first acute angle being smaller than the second acute angle, and the shape of the first cross-section, combine to make the step of insertion and the step of initially thrusting the interbody implant easier than for state of the art fusion cages.

In some embodiments of the method, the instructions include the step of using a guide wire in the step of guiding the interbody implant to the target location. In some embodiments of the method, the instructions include the step of rotating the interbody implant about the nose axis so that an edge surface defining a convex baseline of a cage portion of the interbody implant is arranged for contact with a vertebral end plate proximate the target location.

BRIEF DESCRIPTION OF THE DRAWINGS

FIG. 4 is a plan view of the interbody implant of FIG. 1;

FIG. 5 is an elevational view of a proximal end of the interbody implant of FIG. 1;

FIG. 6 is an elevational view of a lateral side of the interbody implant of FIG. 1;

FIG. 7 is an elevational view of a distal end of the interbody implant of FIG. 1;

FIG. 10 is a sectional view along line X-X of FIG. 6 according to an embodiment of the disclosure;

FIG. 11 is an example of an elliptical cross-section according to an embodiment of the disclosure;

FIG. 12 is an example of an oval cross-section according to an embodiment of the disclosure;

FIG. 13 is an example of an obround cross-section according to an embodiment of the disclosure;

FIG. 14 is a perspective view of an inserter according to an embodiment of the disclosure;

FIG. 15 is a perspective view of the inserter of FIG. 14 being aligned with the interbody implant of FIG. 1 for assembly;

FIG. 26 is a rear perspective view of an interbody implant having a slotted nose portion according to an embodiment of the disclosure:

FIG. 27 is a plan view of the interbody implant of FIG. 26;

FIG. 28 is a sectional view of the interbody implant along plane XXVIII-XXVIII of FIG. 27;

FIG. 32 is a rear perspective view of an interbody implant having a slotted nose portion and a partially slotted rear wall portion according to an embodiment of the disclosure:

FIG. 33 is a plan view of the interbody implant of FIG. 32;

FIG. 34 is a sectional view of the interbody implant along plane XXXIV-XXXIV of FIG. 33;

FIG. 35 is a rear perspective view of an interbody implant having a slotted nose portion and a partially slotted rear wall portion according to an embodiment of the disclosure;

FIG. 36 is a plan view of the interbody implant of FIG. 35; and

FIG. 37 is a sectional view of the interbody implant along plane XXXVII-XXXVII of FIG. 36.

DETAILED DESCRIPTION

Figure 1:
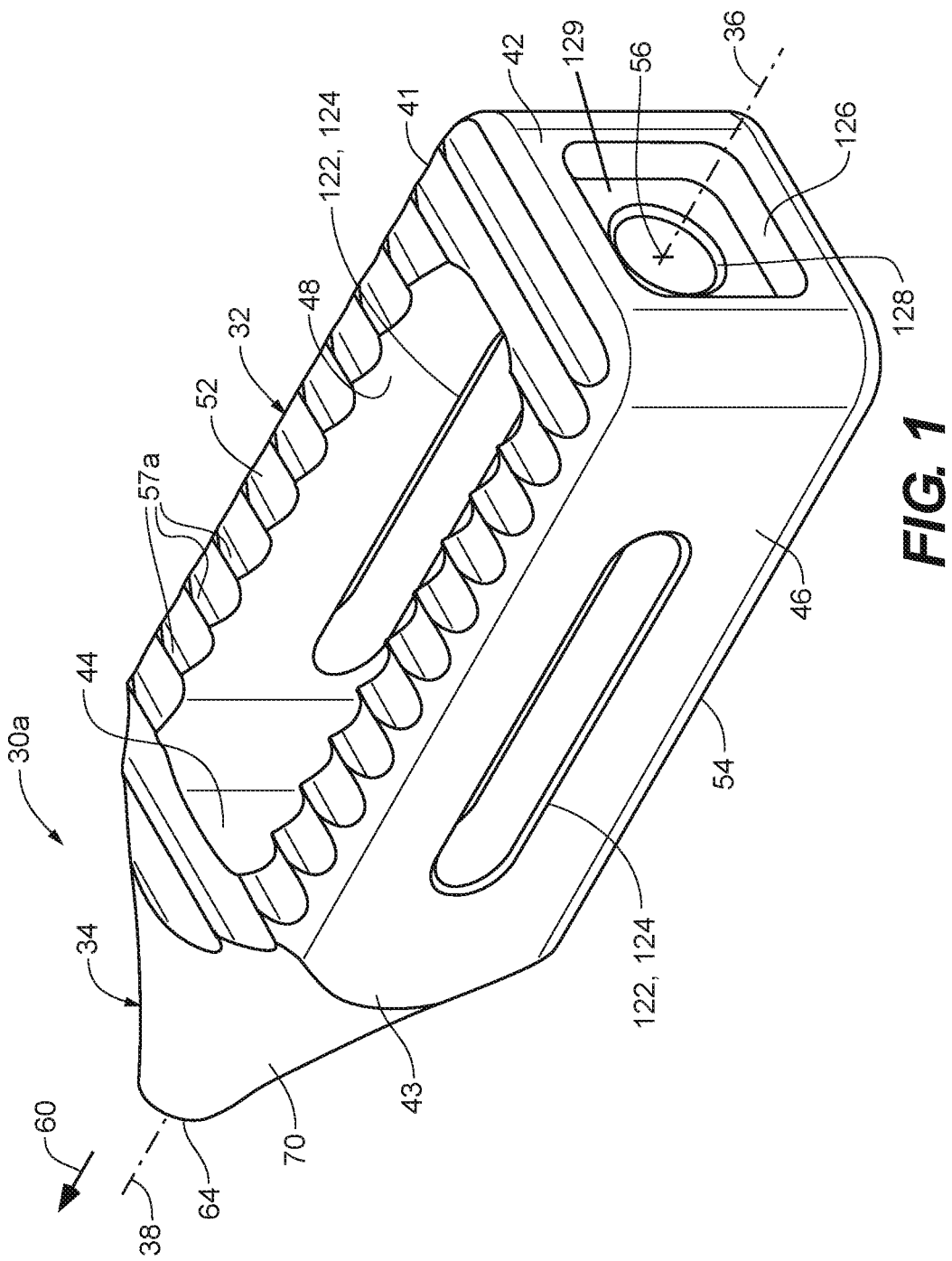
FIGS. 1 through 3 are perspective views of an interbody implant according to an embodiment of the disclosure.
Figure 3:
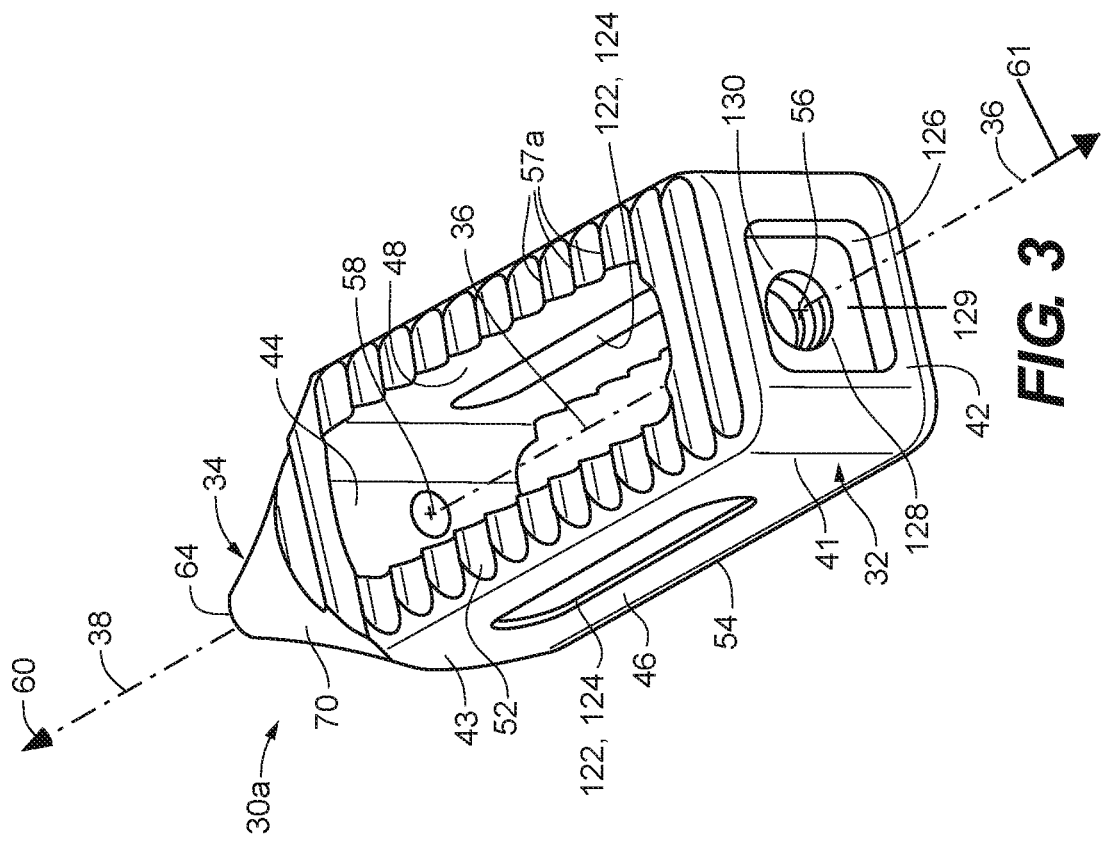
Figure 2:
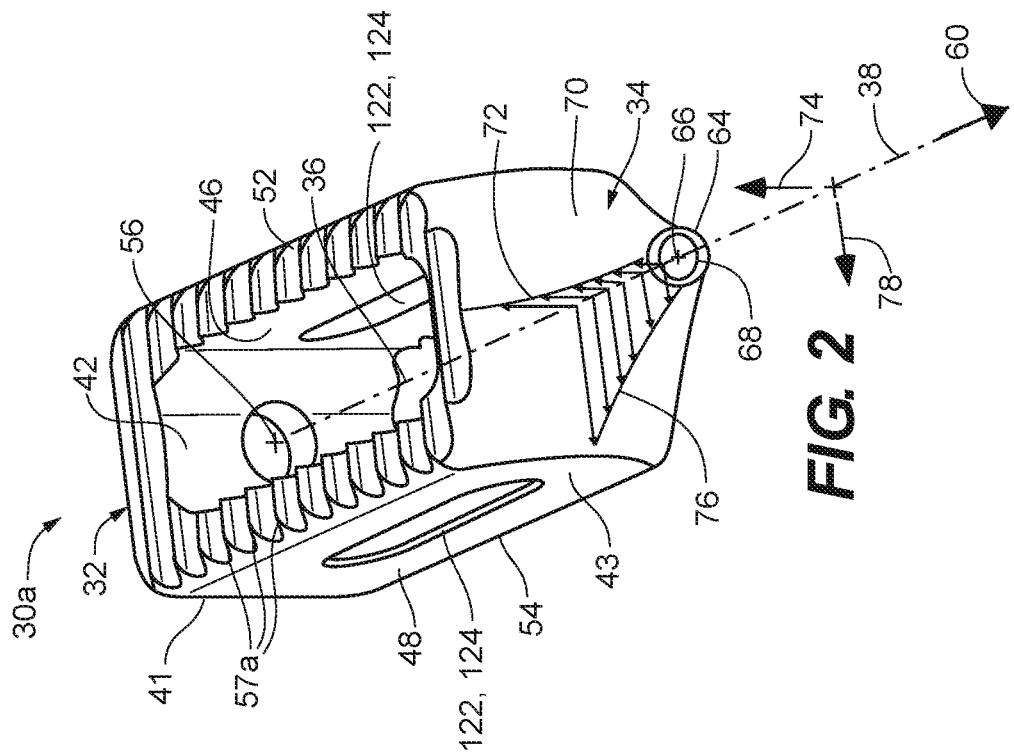

Referring to FIGS. 1 through 9, an interbody implant 30a is depicted according to an embodiment of the disclosure. The interbody implant 30a includes a cage portion 32 and a nose portion 34. The cage portion 32 includes a proximal portion 41 that may include a proximal wall 42 and a distal portion 43 that may include a distal wall 44. In the depicted embodiment, the proximal wall 42 and the distal wall 44 are separated by opposing side walls 46 and 48. The proximal wall 42, distal wall 44, and opposing side walls 46 and 48 cooperate to define opposed edge surfaces 52 and 54. The cage portion 32 defines a cage axis 36 that passes through a center 56 of the proximal wall 42 and a center 58 of the distal wall 44 (FIG. 3). In some embodiments, one or both of the opposed edge surfaces 52, 54 define a plurality of gripping facets 57a extending therefrom.

Figure 8:
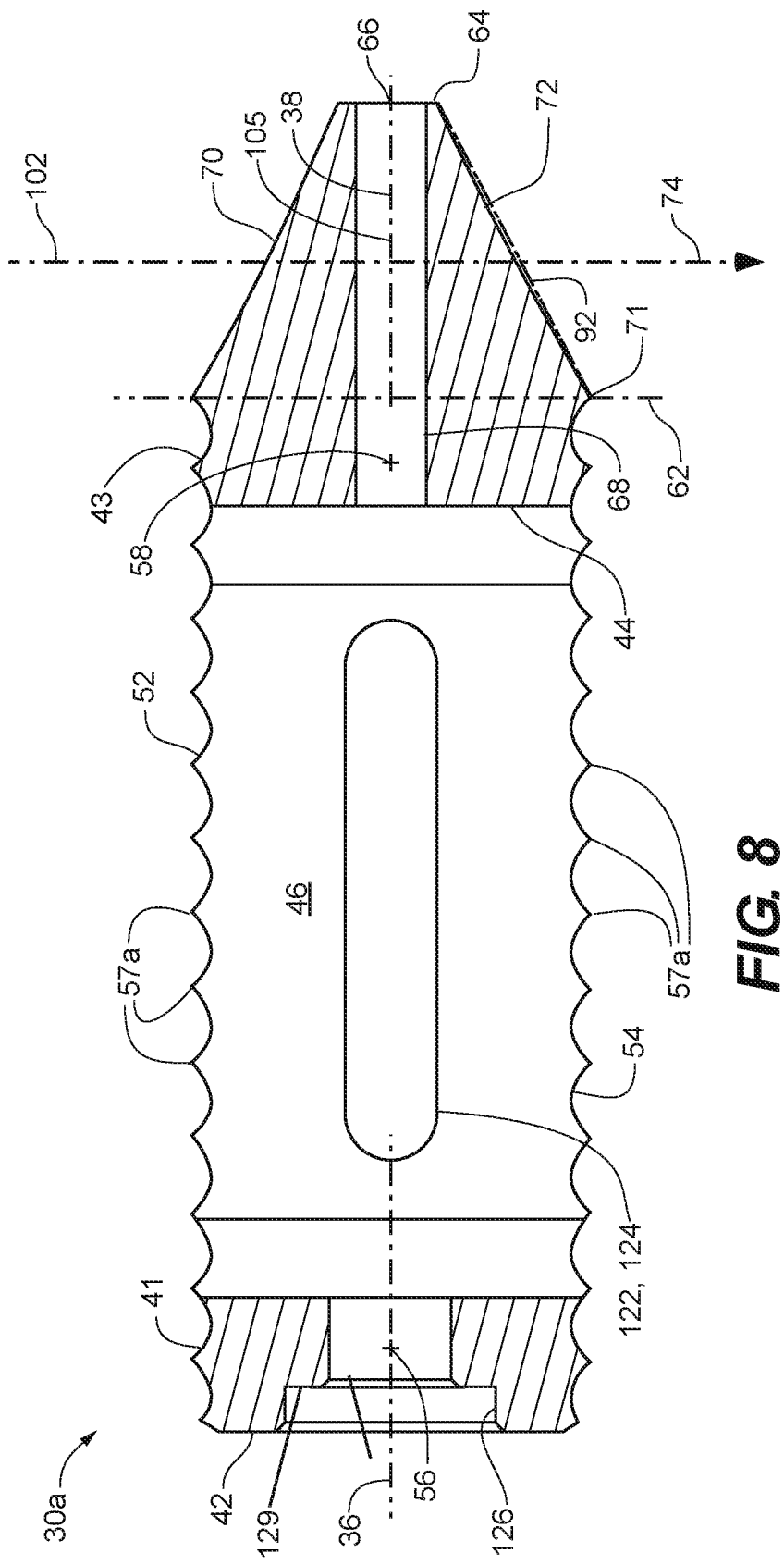
FIG. 8 is a sectional view along line VIII-VIII of FIG. 4 according to an embodiment of the disclosure.

The nose portion 34 extends in a distal direction 60 from the distal portion 43, the nose portion 34 extending from a base plane 62 (FIG. 4) proximate the distal wall 44 of the cage portion 32 to a distal extremity 64. The base plane 62 and the distal extremity 64 are separated by a mid portion 65 of the nose portion 34. The nose portion 34 defines a nose axis 38 that extends from the center 58 of the distal wall 44 through a center 66 of the distal extremity 64. The nose portion 34 further defines an outer surface 70 about the nose axis 38 that tapers toward the nose axis 38 in the distal direction 60. In the depicted embodiment, the nose portion 34 defines a through-passage 68 that is concentric about the nose axis 38. Herein, the base plane 62 passes through a distal-most intersection point 71 of the cage portion 32 and the outer surface 70 of the nose portion 34 and is orthogonal to the nose axis 38 (FIG. 8).

Figure 9:
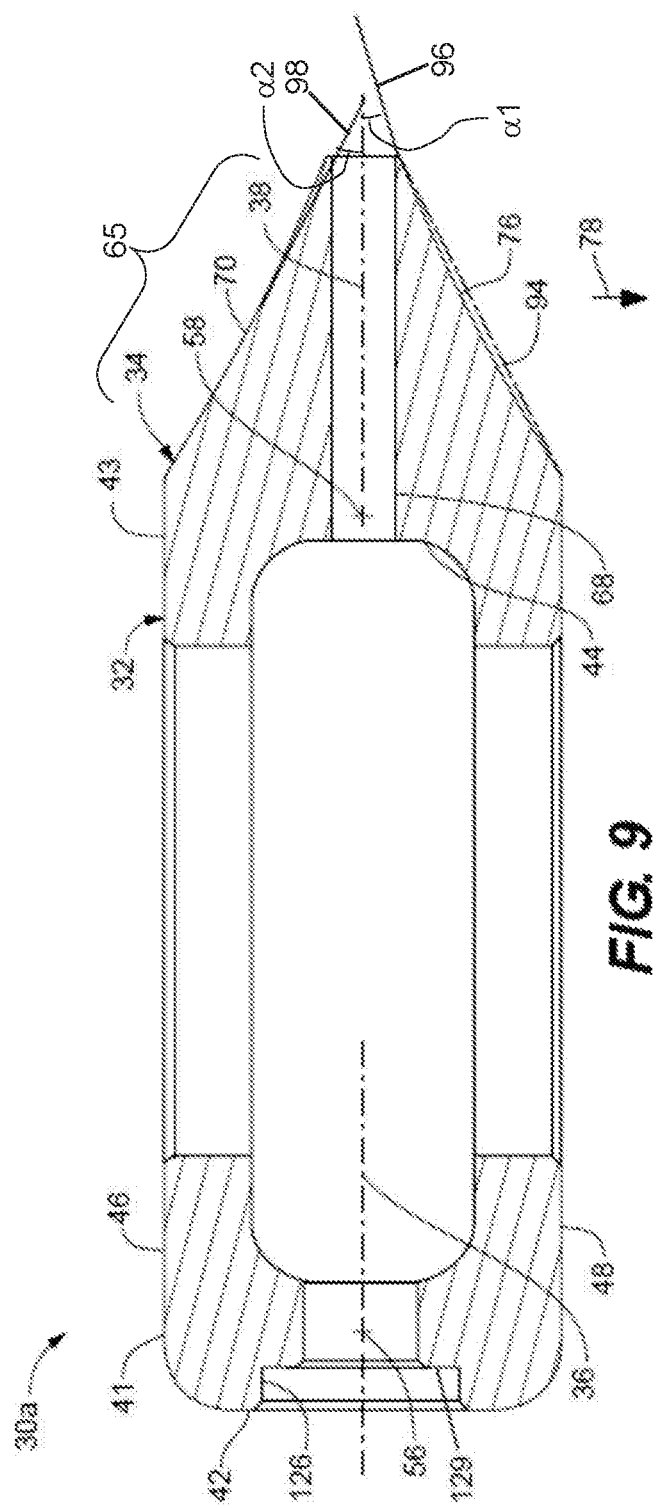
FIG. 9 is a section view along line IX-IX of FIG. 6 according to an embodiment of the disclosure.

In the depicted embodiment, the outer surface 70 defines a first concave profile 72 in a first direction 74 from the from the nose axis 38, the first direction 74 being perpendicular to the nose axis 38. The outer surface 70 of the nose portion 34 may also define a second concave profile 76 in a second direction 78 from the nose axis 38 (FIG. 2), the second direction 78 being perpendicular to the first direction 74 at any point along the nose axis 38. In FIGS. 8 and 9, concavities of the first and second concave profiles 72 and 76 are illustrated by contrasting each with a respective straight line 92 and 94 that passes through the end points of the respective first and second concave profiles 72 and 76. Herein, a first "concavity" of the first concave profile is the maximum dimension between the concave profile 72 and the straight line 92 in a direction perpendicular to the straight line 92. A second "concavity" of the second concave profile is the maximum dimension between the concave profile 76 and the straight line 94 in a direction perpendicular to the straight line 94. The first and second concave profiles 72 and 76 may define different profiles and different concavities.

A characteristic of the concave profiles 72 and 76 is that the slope of the nose portion 34 continuously and monotonically increases in the proximal direction 61, so that not only are the cross-sections orthogonal to the nose axis 38 smaller at the distal extremity 64, the slope defined at the distal extremity 64 is smaller than the slopes defined along the mid portion 65 of the nose portion 34. This characteristic is illustrated for the concave profile 76 of FIG. 9, but applies equally to the concave profile 72 of FIG. 8, as well the concave profile of the nose portion 34 defined at any angular orientation relative to the nose axis 38. In FIG. 9, a slope line 96 is depicted that is representative of the slope of the concave profile 76 at the distal extremity 64, and a slope line 98 is depicted that is representative of the slope of the concave profile 76 at an arbitrary point on the mid portion 65 of the nose portion 34. The slope line 96 at the distal extremity 64 intercepts the nose axis 38 at an acute angle $\alpha 1$, and the slope line 98 at the mid portion 65 intercepts the nose axis 38 at an acute angle $\alpha 2$. The slope line 96 at the distal extremity 64 intercepts the nose axis 38 at a shallower acute angle than does the slope line 98 at the mid portion 65. That is, acute angle $\alpha 1$ is less than acute angle $\alpha 2$.

Functionally, the combination of the smaller cross-sections and smaller acute angles proximate the distal extremity 64 reduces the forces required for the insertion and initial thrusting of the interbody implant 30 during initial location and placement, relative to state of the art fusion cages that have blunted noses of comparatively larger cross-section. The reduced force requirement reduces the difficulty of the insertion and initial thrusting to improve the accuracy of the placement of the interbody implant 30, and reduces or avoids the trauma associated with adjustment or resetting of the implant due to initial misplacement. The circular or oblong shape of the nose cross-sections also makes rotation of the interbody implant 30 easier than with conventional interbody implants that have a square or a rounded-corner square cross-section, thus making rotational orientation of the interbody implant 30 after initial placement easier and less traumatic than rotational orientation of conventional interbody implants.

In the depicted embodiment, the cage and nose axes 36 and 38 of the interbody implant 30a are linear. Because the nose axis 38 is linear, the nose axis 38 is co-planar with both the first concave profile 72 and the second concave profile 76. However, the cage and nose axes 36 and 38 are not so limited. That is, interbody implants are contemplated that have curved cages and nose portions, as disclosed, for example, in U.S. Patent Application Publication No. 2006/0167548 to Jackson. In embodiments where the cage portion or nose portion or both are curved (not depicted herein), the cage and nose axes, being defined by the respective cage and nose portions, are also curved. For a curved nose axis, one of the concave profiles may be co-planar with the curved nose axis, but not both the concave profiles.

Herein, several embodiments of interbody implants are disclosed. The interbody implants are referred to collectively and generically with reference character 30, and specifically and individually with reference character 30 followed by a letter suffix (i.e., interbody implant 30a, discussed above). Likewise, the gripping facets are referred to collectively and generically with reference character 57, and specifically and individually with reference character 57 followed by a letter suffix (i.e., gripping facets 57a).

Referring to FIGS. 10 through 13, cross-sectional profiles 100 and 100a-100c of the outer surface 70 of the nose portion 34 in a cross-section plane 102 that intersects and is orthogonal to the nose axis 38 are depicted according to embodiments of the disclosure. In FIG. 10, the cross-section plane 102 intersects the nose axis 38 at a midpoint 105 (cross-section plane 102 and midpoint 105 both depicted in FIG. 8) along the nose axis 38 that is equidistant between the base plane 62 and the distal extremity 64. Generally, the outer surface 70 of the nose portion 34 includes rounded surfaces having cross-sections that defined little or no adjacent straight portions that require corner transitions. Such rounded surfaces may define a circular cross-section (not depicted) or oblong cross-sections 104. Herein, an "oblong" cross section is one that defines a maximum or major dimension 106 and a minor or minimum dimension 108, the minor dimension 108 being perpendicular to the major dimension 106. Specific and non-limiting examples of an oblong cross-section are an ellipse 104a (i.e., substantially defined by the mathematical equation for an ellipse, as in FIG. 11), an oval 104b (i.e., "egg-shaped," as in FIG. 12), and an obround 104c (i.e., straight line segments that are parallel with hemispherical ends, as in FIG. 13). It is noted that the obround cross-section 104c includes flats, but being parallel, do not define a corner that must be transitioned. Herein, the oblong cross-sections are referred to collectively or generically by numerical reference 104, while specific or individual oblong cross-sections are by a letter suffix following the numerical reference 104 (e.g., the elliptical cross-section 104a).

In some embodiments, the oblong cross-section 104 is continuously curved. Herein, a "continuously curved" oblong cross-section does not include any linear segments. Accordingly, the elliptical cross-section 104a and the oval cross-section 104b are continuously curved, whereas the obround cross-section is not continuously curved.

In some embodiments, the oblong cross-section 104 is axisymmetric. Herein, for an "axisymmetric" cross-section, any line 112 that passes through a center point 110, regardless of direction, also defines diametrically opposed intersection points 114 and 116 that are equidistant from the center point 110, as illustrated for the obround cross-section 104c (FIG. 13). Accordingly, the elliptical cross-section 104a and the obround cross-section 104c are axisymmetric, whereas the oval cross-section 104b is not axisymmetric.

The oblong cross-sections 104 may be characterized by a ratio R of the major dimension to the minor dimension. In some embodiments, the ratio R is in a range of 1.05 to 1.20 inclusive. Herein, a range that is said to be "inclusive" includes the stated end point values of the range and all values therebetween. In some embodiments, the ratio R is in a range of 1.05 to 1.15 inclusive. In some embodiments, the ratio R is in a range of 1.07 to 1.12 inclusive.

Referring again to FIGS. 1 through 9, each of the opposing side walls 46 and 48 may define a side graft window 122 that passes therethrough. The side graft window 122 may define an elongate slot 124 ("elongate" being defined as having a major and a minor dimension, the major dimension defining an "elongate" direction). The elongate slot 124 may extend substantially parallel to the cage axis 36. In various embodiments, the proximal wall 42 defines an exterior recess 126 bounded by a distal face 129 that faces in a proximal direction 61 (FIG. 3). The proximal wall 42 may further define a through-hole 128 that extends distally from the distal face 129 of the exterior recess 126 and is concentric about the cage axis 36. The through-hole 128 may be tapped to define interior threads 130 (FIG. 3). The exterior recess 126 may be polygonal (e.g., triangular, square, rectangular, hexagonal, octagonal).

In some embodiments, the outer surface 70 of the nose portion 34 may have the geometric characteristics of a one-sheeted hyperboloid—i.e., concave (hyperbolic) profiles that may define different shapes (different hyperbolas) in directions that are perpendicular to each other, the hyperbolic surface defining oblong (elliptical) cross-sections along a central axis. One sheeted hyperboloids are described, for example, by Weisstein, Eric W. "One-Sheeted Hyperboloid", from MATHWORLD—A WOLFRAM WEB RESOURCE (available at http://mathworld.wolfram.com/One-SheetedHyperboloid.html, last visited Dec. 7, 2016), the disclosure of which is incorporated by reference herein except for any express definitions contained therein. Of course, while the disclosed outer surface 70 of the nose portion 34 may include a portion that has these general characteristics, strict adherence to any mathematical formulae is optional.

In various embodiments, the interbody implant 30 is fabricated from biologically inactive materials, which may be metallic or non-metallic. Metallic biologically inactive materials may include certain stainless steel alloys, titanium, tantalum, or other alloys and materials which are structurally, chemically, and biologically appropriate. Non-metallic biologically inactive materials include certain plastics or polymers, organic and inorganic resins, composites, and ceramics, (e.g., polyester ketone or polyether ether ketone). The polymers may be non-porous. The composites may include carbon fiber reinforced materials. Appropriate ceramics may be porous and can be of an "open scaffold" type which allow bone fusion growth through the ceramic material itself.

Referring to FIGS. 14 through 19, an inserter 150 for inserting an interbody implant 30 is depicted according to an embodiment of the disclosure. The inserter 150 includes a shaft assembly 152 having a proximal end 154 and a distal end 156. The shaft assembly 152 may include an inner shaft 162 rotatable and translatable within an outer sheath 164 and about an actuation axis 158 of the inserter 150. The outer sheath 164 may include telescoping tubes 168. In the depicted embodiment, the inner shaft 162 defines the distal end 156 of the shaft assembly 152 and is coupled to a knob 166 at the proximal end 154 of the shaft assembly 152. A handle assembly 170 may be coupled to the outer sheath 164 at the proximal end 154 of the shaft assembly 152. In the depicted embodiment, the handle assembly 170 includes a T-shaped handle 171. Also in the depicted embodiment, a guide wire passage 172 is defined that is concentric about the actuation axis 158 and passes through the knob 166, the inner shaft 162, and the distal end 156 of the inserter 150. In some embodiments, a channeled knob 166a is utilized as the knob 166, the channeled knob 166a defining at least one radially extending channel 169 that extends from the guide wire passage 172.

In the depicted embodiment, a mounting interface 180 is disposed at the distal end 156. The mounting interface 180 includes a boss 182 configured for complementary insertion into the recess 126 of the proximal wall 42 of the interbody implant 30. The boss 182 is coupled to the outer sheath 164 and configured so that the inner shaft 162 is rotatable within the boss 182. In some embodiments, a threaded tip 184 is formed on or otherwise coupled to the distal end 156 of the inner shaft 162, for threaded engagement with the interior threads 130 of the through-hole 128.

Figure 16:
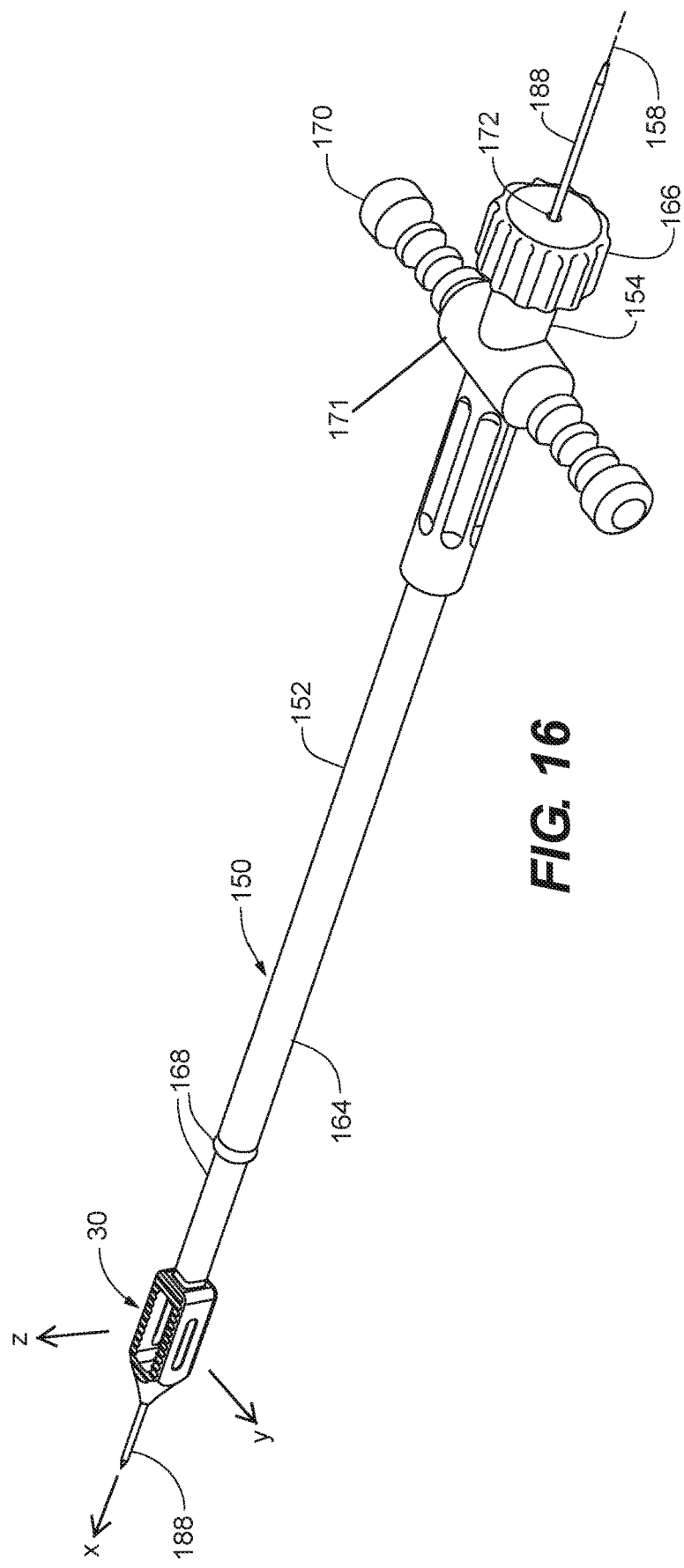
FIG. 16 is a perspective view of the inserter and interbody implant of FIG. 15 in assembly.
Figure 17:
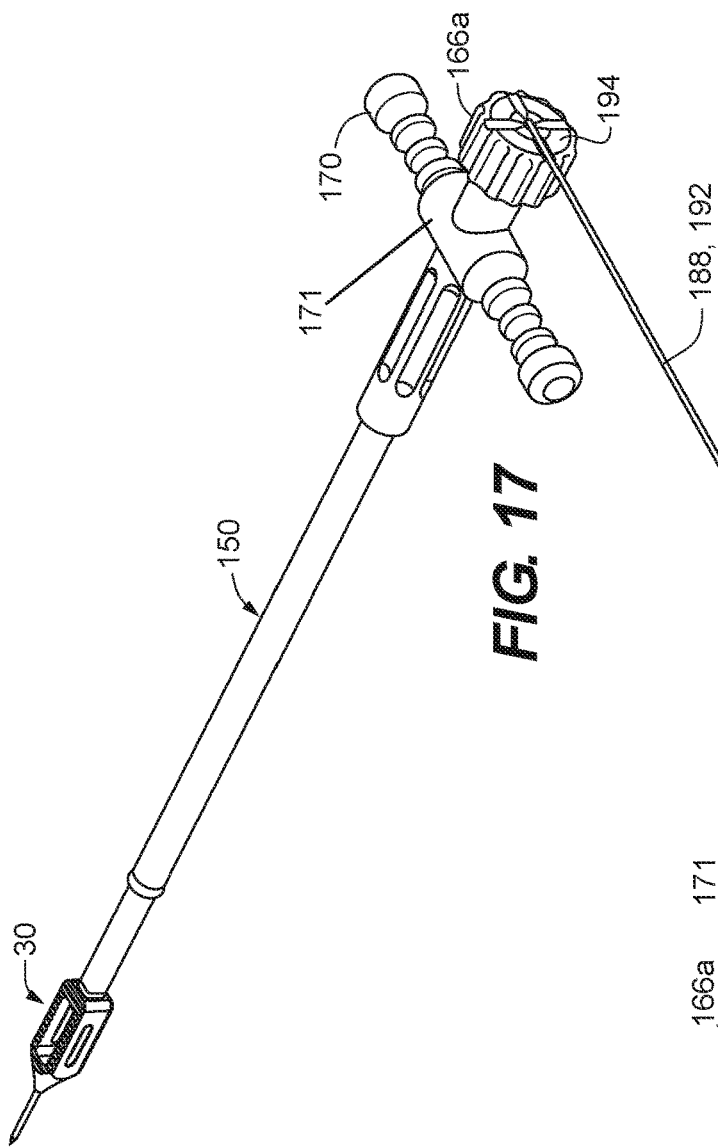
FIG. 17 is a perspective view of the inserter of an inserter having a channeled knob, with interbody implant of FIG. 1 in assembly according to an embodiment of the disclosure.
Figure 19:
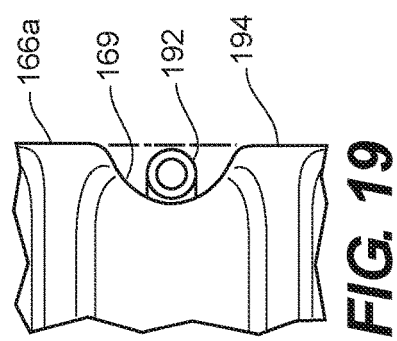
FIG. 19 is an enlarged, partial side view of a guide wire recessed within a channel of the channeled knob of FIG. 17.
Figure 18:
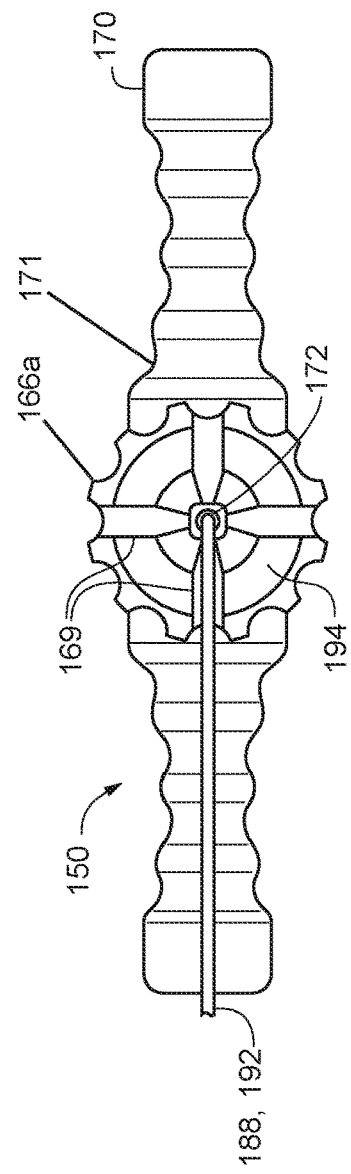
FIG. 18 is a proximal end view of the inserter with the channeled knob of FIG. 17.

In operation, the interbody implant 30 is aligned with the mounting interface 180 and the boss 182 is inserted into the recess 126. The threaded tip 184 is screwed into the interior threads 130 by rotating the inner shaft 162 with the knob 166. Once the interbody implant 30 is affixed to the distal end 156 of the inserter 150, the implant 30 can be manipulated with the handle assembly 170 by grasping the T-shaped handle 171. A guide wire 188, such as a Kirschner or "K-wire," may be inserted into the guide wire passage 172, through the knob 166, inner shaft 162, mounting interface 180, and the through-passage 68 of the interbody implant 30, the guide wire 188 extending distal to the distal extremity 64 of the interbody implant 30 (FIG. 16). For embodiments implementing the channeled knob 166a, the guide wire 188 may be folded away from the 158 actuation axis so that a folded end 192 of the guide wire 188 is routed through the radially extending channel 169 (FIGS. 17-19) once the guide wire 188 is positioned within the patient. The radially extending channel(s) 169 may be configured so that the folded end 192 of the guide wire 188 is recessed from a proximal surface 194 of the channeled knob 166a (FIG. 19).

Functionally, the boss 182 provides rotation control of the interbody implant 30 by manipulating the inserter 150 with the handle assembly 170. The T-shaped handle 171 provides gripping of the handle assembly 170 that enables the user a full range of manipulation of the inserter 150 and implant 30: translation along and roll about the x-axis, pitch about the y-axis, and yaw about the z-axis (FIG. 16). The guide wire 188 helps locate and guide the interbody implant 30 to the desired implant location. Upon achieving the desired insertion of the interbody implant 30 into a spine of a patient, the inserter 150 may be decoupled from the interior threads 130 of the through-passage 128 by retracting the guide wire 188 proximally through the inserter 150 and unscrewing threaded tip 184 from the through-hole 128 with the knob 166. The folding of the guide wire 188 and positioning of the folded end 192 within the radially extending channel 169 enables a surgeon to tamp the proximal face 194 of the channeled knob 166a without directly impacting the guide wire 188, thereby preventing damage to both the guide wire 188 and the channeled knob 166a.

Figure 20:
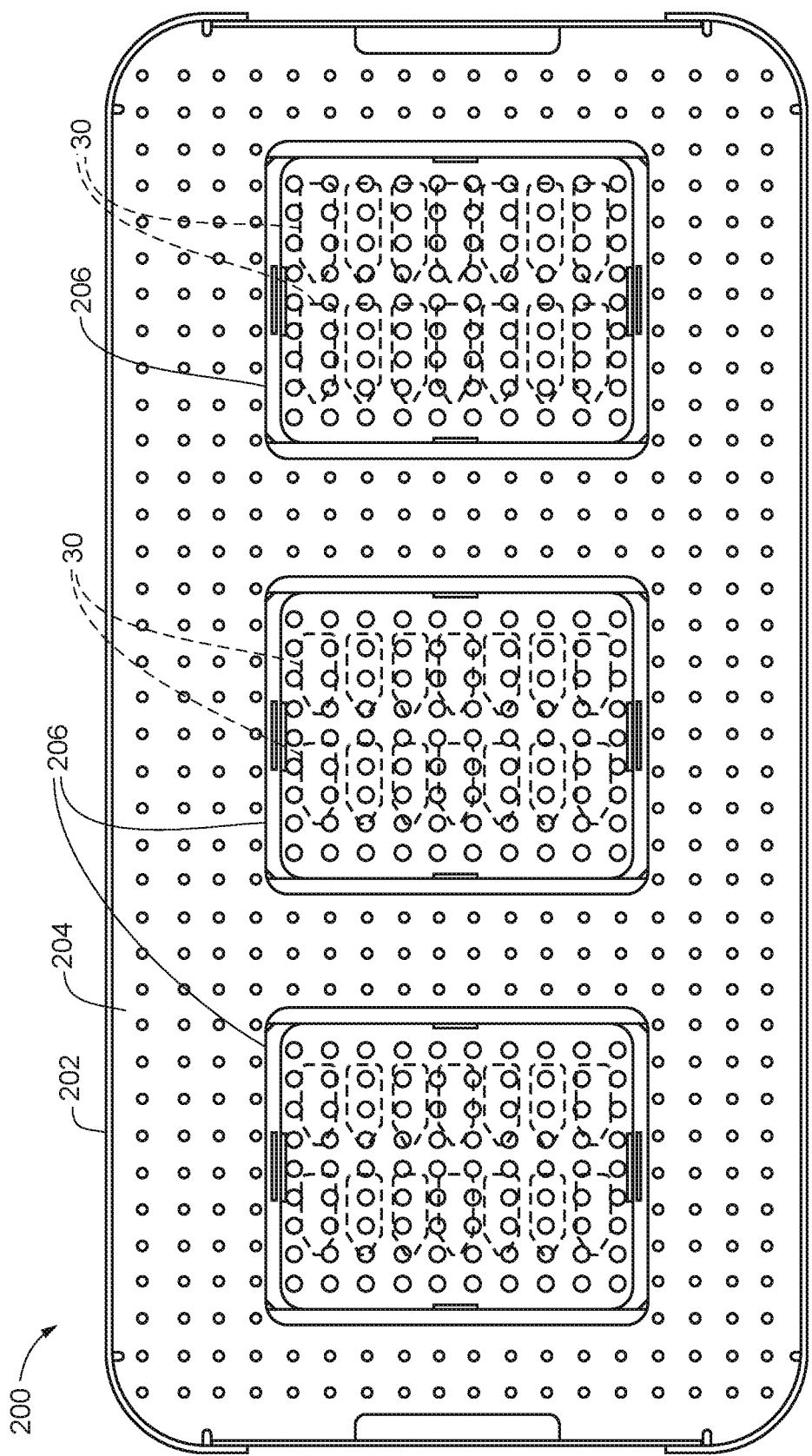
FIG. 20 is a plan view of a tray for a kit that includes caddies with a variety of interbody implants according to an embodiment of the disclosure.
Figure 21:
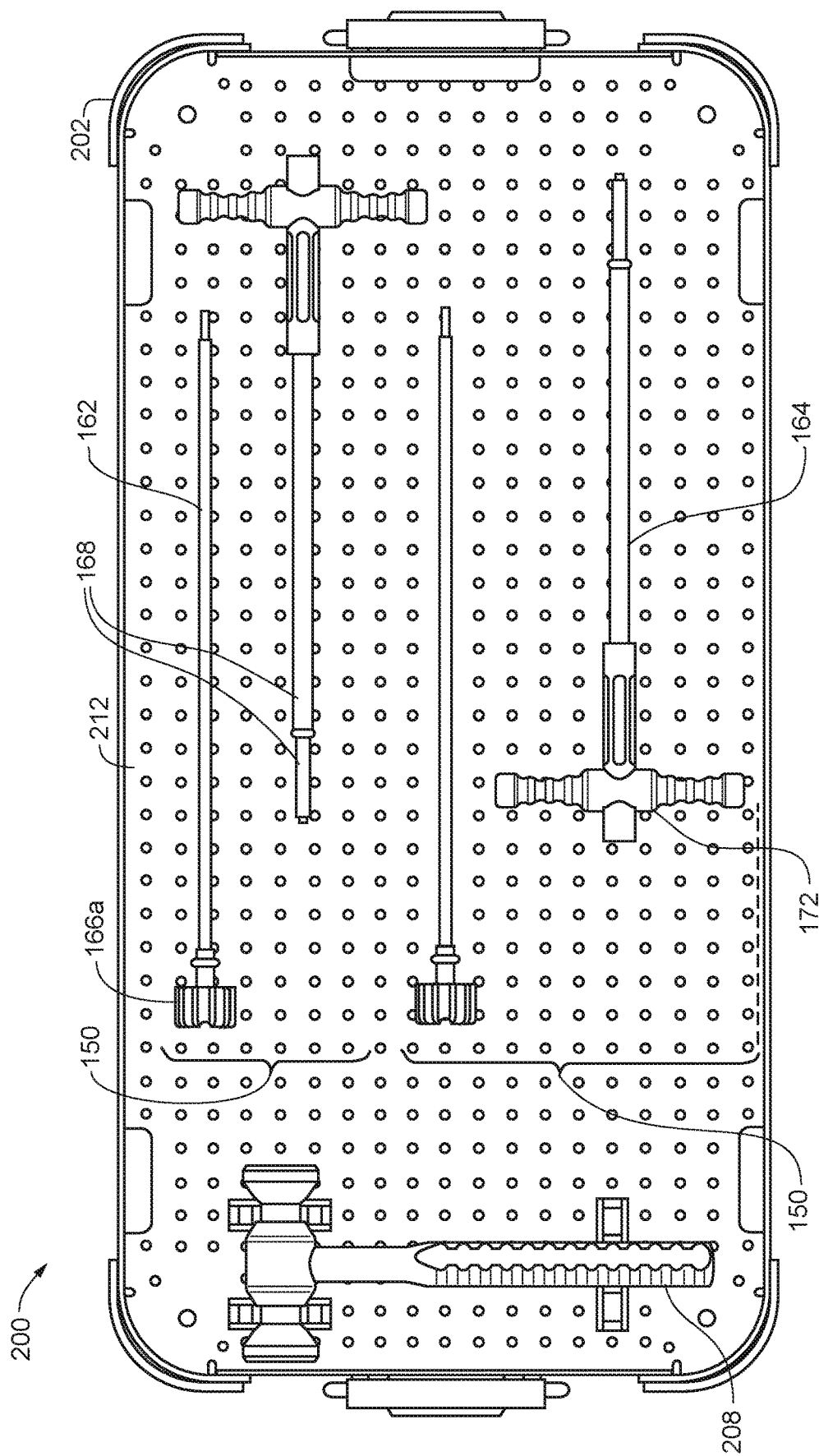
FIG. 21 is a plan view of an instrument tray for a kit according to an embodiment of the disclosure.
Figure 23:
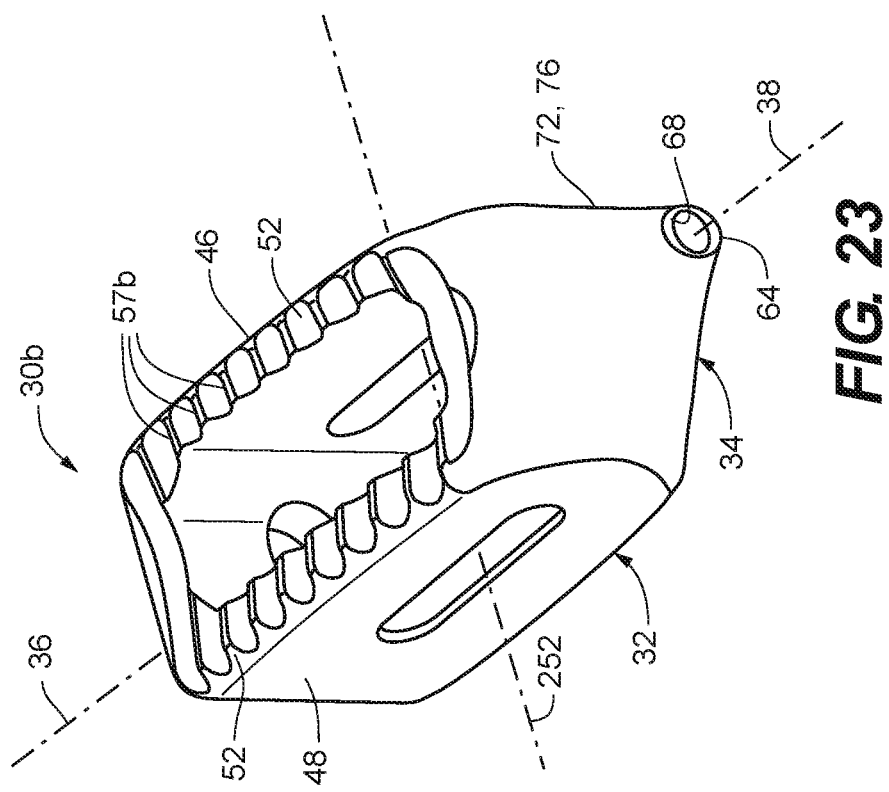
FIG. 23 is a front perspective view of the interbody implant of FIG. 22.
Figure 22:
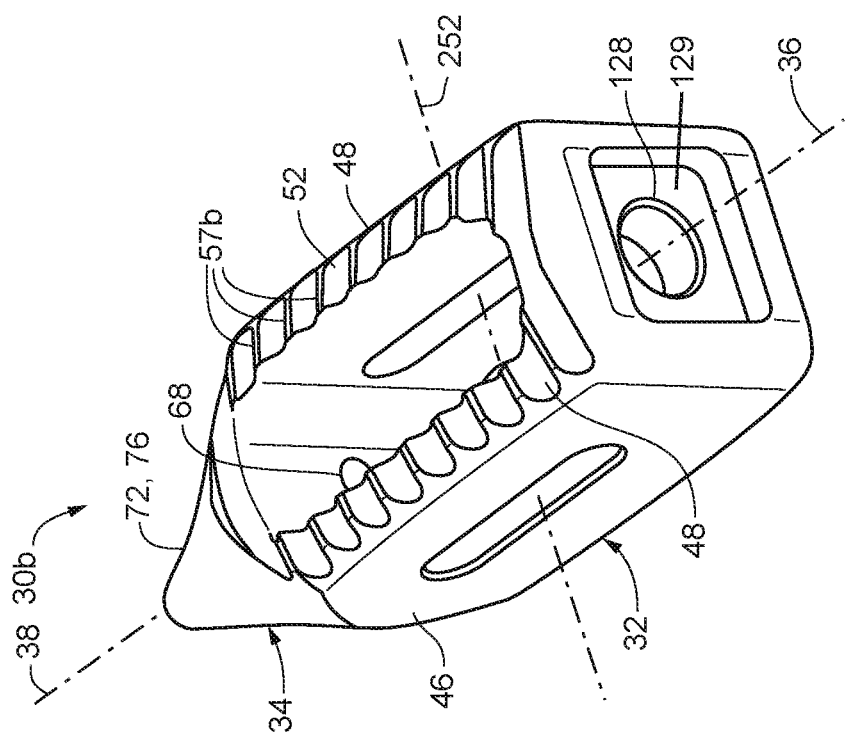
FIG. 22 is a rear perspective view of an interbody implant having convex superior and inferior surfaces according to an embodiment of the disclosure.

Referring to FIGS. 20 and 21, an interbody implant kit 200 is depicted in an embodiment of the disclosure. The kit 200 may include a case 202 that holds a tray 204 having caddies 206, each caddy 206 including a selection of interbody implants 30 of different sizes. Each caddy 260 may hold implants of uniform length, for example, one of 27 mm, 30 mm, or 33 mm. An example and non-limiting width of the implants is 9.5 mm. In some embodiments, each caddy 206 includes paired implants of various heights, for example, heights of 9 mm, 10 mm, 11 mm, 12 mm, 13 mm, 14 mm, and 15 mm. a pair of each height implant, with implant. Herein, "height" refers to the dimension that is generally in the superior/inferior direction of an implanted implant, "length" refers to the dimension that is generally in the posterior/anterior direction of an implanted implant, and "width" refers to the dimension that is generally in the lateral direction of an implanted implant.

In some embodiments, the kit 200 includes one or more inserters 150, as well as a tamping hammer 208, mounted to a tray 212 that also fits within the case 202. The kit 200 may also include non-transient instructions on a tangible medium (e.g., on a paper document, compact disk, flash drive) for assembly and operation of the inserter 150 and interbody implant 30.

The kit 200 may also include instructions for implantation of the interbody implants 30, the instructions being on a tangible, non-transitory medium (e.g., a printed document or a computer readable medium such as a compact disk, flash drive, or hard drive).

Referring to FIGS. 22 through 25, an interbody implant 30b is depicted according to an embodiment of the disclosure. The interbody implant 30b includes many of the same components and attributes as the interbody implant 30a, which are indicated with same-numbered reference characters. In addition, the opposed edge surfaces 52, 54 of the interbody implant 30b each define a convex baseline 250 that is arcuate about a lateral axis 252, the lateral axis 252 being perpendicular to the cage axis 36. In some embodiments, gripping facets 57b project outward from (i.e., away from the lateral axis 252) the convex baselines 250.

Figure 24:
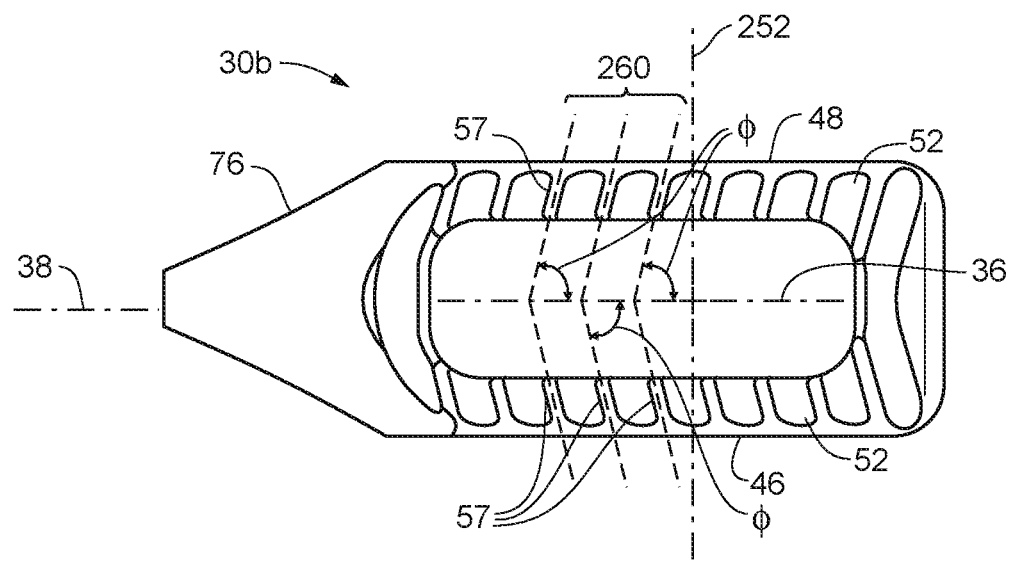
FIG. 24 is a plan view of the interbody implant of FIG. 22.
Figure 25:
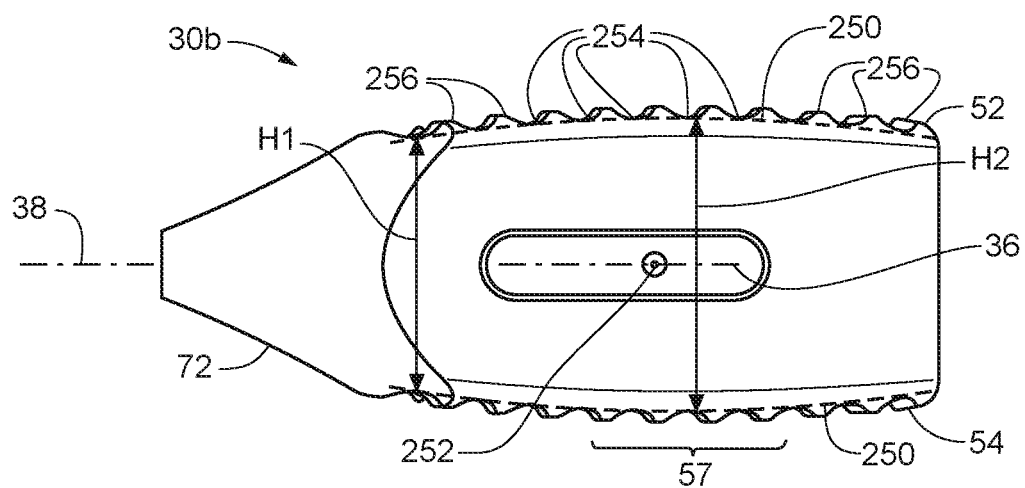
FIG. 25 is a side elevational view of the interbody implant of FIG. 22.

Herein, a "baseline" of the edge surfaces 52, 54 is a datum that passes through the local minima 254 located between proud projections 256 of the gripping facets 57 (depicted with dashed lines in FIG. 25). The convex baseline 250 may be characterized by a minimum height H1 and a maximum height H2 of the opposing side walls 46 and 48. In some embodiments dimension of the convexity of the convex baseline (H2–H1) is in a range of 1 mm to 5 mm inclusive; in some embodiments dimension of the convexity of the convex baseline (H2–H1) is in a range of 2 mm to 4 mm inclusive. In some embodiments, each of the plurality of gripping facets 57b defines a ridge 258 that extends along a ridge line 260, as depicted at FIG. 24. The ridge line 260 extends proximally at a swept angle φ relative to the cage axis 36, the swept angle φ defining an acute angle relative to the cage axis 36.

Functionally, the convex baselines 250 of the opposed edge surfaces 52, 54 better conform to the concave endplates of the vertebrae to which the interbody implant 30b is engaged. Because the convex baseline 250 is more complementary to the concave shape of the end plate of the engaged vertebrae, the load imposed between the vertebrae and the interbody implant 30b is distributed over a greater area, thus avoiding stress concentrations at the interface of the interbody implant 30b and the vertebral endplates. In this way, tissue growth between the interbody implant 30b occurs faster and more uniformly than with conventional implants having planar superior and inferior baseline surfaces. The swept angles 4 of the gripping facets 57b may reduce the resistance to insertion of the interbody implant 30b relative to the resistance of withdrawal of the interbody implant 30b, thereby favoring retention while easing implantation of the interbody implant 30b. Accordingly, the retention characteristics of the gripping facets 57b do not rely on projections that define a relatively sharp edge, so the tops of the gripping facets 57b may be blunted.

Referring to FIGS. 26 through 28, an interbody implant 30c is depicted according to an embodiment of the disclosure. The interbody implant 30c may include many of the same components and attributes as the interbody implant 30b, which are indicated with same-numbered reference characters. In addition, the nose portion 34 of the interbody implant 30c defines a forward or distal slot 270 that extends from the through-passage 68 of the nose portion 34 in one direction and through the outer surface 70 of the nose portion 34, as depicted in FIG. 28. The distal slot 270 is coplanar with the nose axis 38 and defines a gap dimension 272 that is less than a minimum diameter 274 of the through-passage 68.

Figure 30:
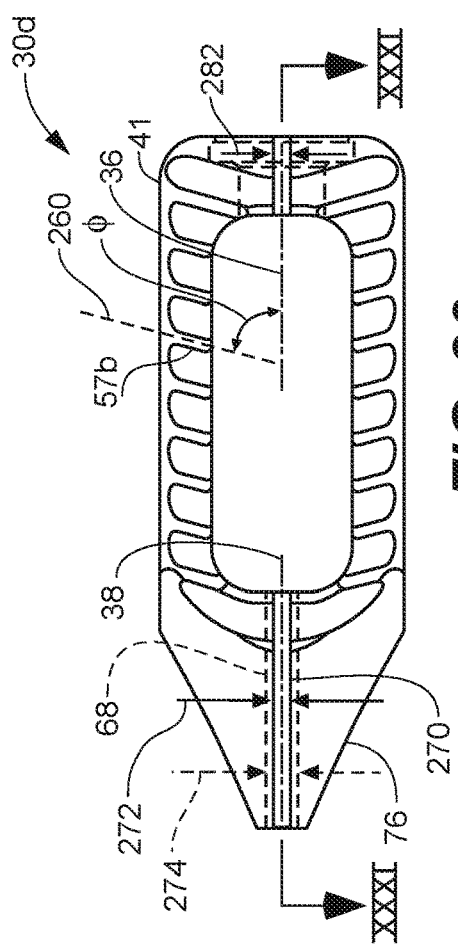
FIG. 30 is a plan view of the interbody implant of FIG. 29.
Figure 31:
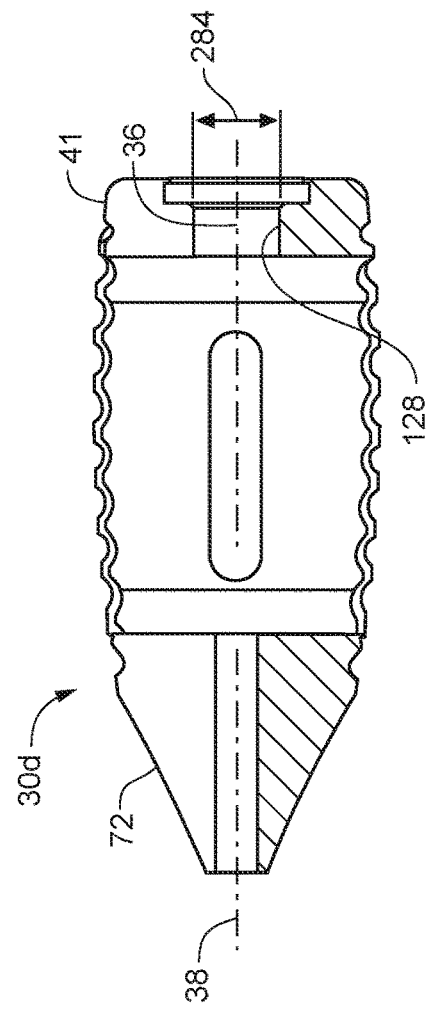
FIG. 31 is a sectional view of the interbody implant along plane XXXI-XXXI of FIG. 30.
Figure 29:
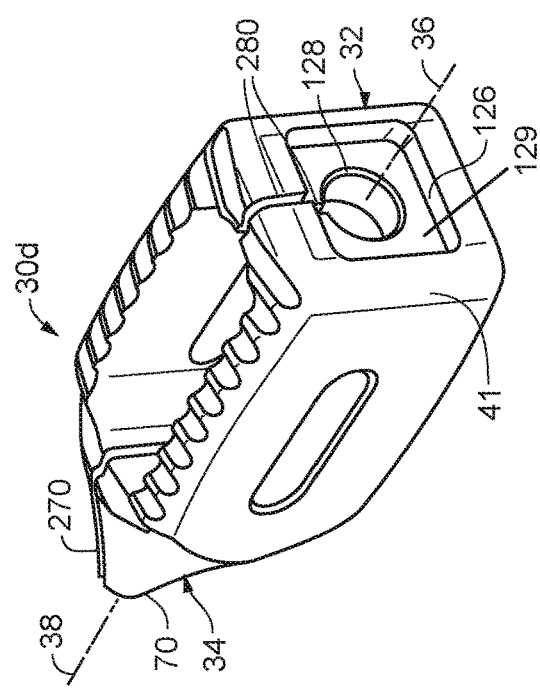
FIG. 29 is a rear perspective view of an interbody implant having a slotted nose portion and a slotted rear wall portion according to an embodiment of the disclosure.

Referring to FIGS. 29 through 31, an interbody implant 30d is depicted according to an embodiment of the disclosure. The interbody implant 30d may include many of the same components and attributes as the interbody implants 30b and 30c, which are indicated with same-numbered reference characters. In addition, the cage portion 32 of the interbody implant 30d defines a rearward or proximal slot 280 that extends from the through-passage 128 of the cage portion 32 in one direction and through the outer surface of the proximal portion 41 (FIGS. 29 and 31). The proximal slot 280 may be coplanar with the cage axis 36. In some embodiments, the proximal slot 280 defines a gap dimension 282 that is less than a minimum diameter 284 of the through-passage 128.

Referring to FIGS. 32 through 34, an interbody implant 30e is depicted according to an embodiment of the disclosure. The interbody implant 30e includes many of the same components and attributes as the interbody implant 30d, which are indicated with same-numbered reference characters. A modification to the interbody implant 30e relative to the interbody implant 30d is that the proximal slot 280, while still coplanar with the cage axis 36, does not extend from the through-passage 128 of the cage portion 32. Rather, a ring or surround 288 of material is continuous about through-passage 128, as depicted in the cross-section of the proximal portion 41 in FIG. 34.

Referring to FIGS. 35 through 37, an interbody implant 30f is depicted according to an embodiment of the disclosure. The interbody implant 30f includes many of the same components and attributes as the interbody implant 30e, which are indicated with same-numbered reference characters. A modification to the interbody implant 30f relative to the interbody implant 30e is presence of ribs 292 that bridge the distal slot 270. In the depicted embodiment, the ribs 292 are flush with the diameter of the through-passage 68, so that the cross section of the through-passage 68 is continuous about the nose axis 38 at the location of the ribs 292. The ribs 292 may be disposed at the distal wall 44 of the cage portion 32 and at the distal extremity 64 of the nose portion 34 (depicted).

Functionally, the distal and proximal slots 270 and 280 provide additional paths for tissue to grow into and through the interbody implant 30, thus promoting a faster and more secure fusion between the vertebrae. For the interbody implant 30e, the surround 288 of material reinforces the through-passage 128 to maintain the integrity of the recess 126 under the torsion that may be applied to the interbody implant 30e during implantation. The ribs 292 prevents the guide wire 188 from entering and becoming jammed in the distal slot 270.

The interbody implants 30 depicted herein include a variety of combinations that are non-essential. For example, the interbody implants depict gripping facets 57 on both the of the opposed edge surfaces 52, 54; embodiments are contemplated wherein gripping facets 57 are provided on only one of the opposed edge surfaces 52, 54. The interbody implants 30b through 30f depict both of the opposed edge surfaces 52 and 54 as defining the convex baseline 250; embodiments are contemplated wherein the convex baseline 250 is defined by only one of the opposed edge surfaces 52 or 54. The interbody implants 30c through 30f are depicted as including distal and proximal slots 270 and 280 that are co-planar; embodiments are contemplated where the distal and proximal slots are not co-planar. The co-planar slots 270 and 280 are disclosed as defining gap dimensions 272 and 282, respectively, that are less than a minimum diameter 284 of the through-passage 128; embodiments are contemplated where one or both of the gap dimensions 272 and 282 are the same or greater than the minimum diameter 284 of the through-passage 128. The interbody implant 30f depicts two ribs 292 that bridge the distal slot 270; a single rib 292 bridging the distal slot 270 is also contemplated, for example at the distal wall 44 only, the distal extremity 64 only, or at a location therebetween.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

The following documents are incorporated by reference herein in their entirety: U.S. Patent Application Publication No. 2006/0167548 to Jackson; U.S. patent application Ser. No. 29/593,823 to Abbasi entitled "Spinal Fusion Cage", filed Feb. 13, 2017; U.S. patent application Ser. No. 29/608,791 to Abbasi entitled "Spinal Fusion Cage", filed Jun. 26, 2017. Incorporation by reference of these documents is limited such that no subject matter is incorporated that is contrary to the explicit disclosure herein. Any incorporation by reference of documents above is further limited such that no claims included in the documents are incorporated by reference herein. Any incorporation by reference of documents is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. An interbody implant, comprising:
   a cage portion defining a cage axis that passes through a proximal portion and a distal portion thereof; and a nose portion extending in a distal direction from the distal portion of the cage portion, the nose portion defining a nose axis that is concentric with the cage axis, the nose axis extending in the distal direction from the cage portion through a distal extremity of the nose portion, the nose portion defining an outer surface about the nose axis that tapers toward the nose axis in the distal direction, the outer surface defining a first concave profile in a first direction from the nose axis, the first direction being perpendicular to the nose axis, the outer surface of the nose portion defining a second concave profile in a second direction from the nose axis, the second direction being perpendicular to the first direction at any point along the nose axis.

2. An interbody implant, comprising:
a cage portion defining a cage axis that passes through a proximal portion and a distal portion thereof; and
a nose portion extending in a distal direction from the distal portion of the cage portion, the nose portion defining a nose axis that is concentric with the cage axis, the nose axis extending in the distal direction from the cage portion through a distal extremity of the nose portion, the nose portion defining an outer surface about the nose axis that tapers toward the nose axis in the distal direction,
wherein:
the nose portion defines a through-passage concentric about the nose axis, the through-passage defining a minimum diameter; and
the nose portion defines a first slot that extends from the through-passage through an exterior surface of the nose portion, the first slot being in fluid communication with the through-passage, the first slot being coplanar with the nose axis and defining a gap dimension that is less than the minimum diameter of the through-passage of the nose portion.

3. The interbody implant of claim 2, comprising a second slot that extends through an outer surface of the proximal portion of the cage portion, the second slot being coplanar with the cage axis.

4. The interbody implant of claim 3, wherein the first slot and the second slot are coplanar.

5. The interbody implant of claim 2, comprising a rib that bridges the first slot proximate the through passage of the nose portion.

6. The interbody implant of claim 5, wherein the rib is disposed at one of the distal portion of the cage portion and the distal extremity of the nose portion.

7. The interbody implant of claim 2, wherein the outer surface defines a first concave profile in a first direction from the nose axis, the first direction being perpendicular to the nose axis.

8. The interbody implant of claim 7, wherein the outer surface of the nose portion defines a second concave profile in a second direction from the nose axis, the second direction being perpendicular to the first direction at any point along the nose axis.

9. The interbody implant of claim 8, wherein the outer surface of the nose portion defines an oblong cross-section at a cross-section plane that intersects and is orthogonal to the nose axis, the oblong cross section defining a major dimension and a minor dimension, the minor dimension being perpendicular to the major dimension.

10. The interbody implant of claim 9, wherein the oblong cross-section is continuously curved.

11. The interbody implant of claim 10, wherein the oblong cross-section is elliptical.

12. The interbody implant of claim 9, wherein the cross-section plane intersects the nose axis at a midpoint that is equidistant between the base plane and the distal extremity.

13. The interbody implant of claim 7, wherein the first concave profile and the nose axis are co-planar.

14. The interbody implant of claim 13, wherein the second concave profile and the nose axis are co-planar.

15. The interbody implant of claim 13, wherein the first concave profile is different from the second concave profile.

16. The interbody implant of claim 15, wherein the first concave profile defines a first concavity, the second concave profile defining a second concavity, the first concavity being greater than or less than the second concavity.

17. The interbody implant of claim 2, wherein the nose portion extends from a base plane proximate the distal portion of the cage portion, the base plane being orthogonal to the nose axis.

18. The interbody implant of claim 2, wherein the outer surface of the nose portion is axisymmetric about the nose axis.

19. The interbody implant of claim 2, wherein the interbody implant is titanium.

20. An interbody implant for treatment of a spine, comprising:
an interbody implant including a nose portion defining a nose axis, the nose portion having a distal extremity and a mid portion, the distal extremity defining a first cross-section that is orthogonal to the nose axis, the nose portion including an outer surface that is axisymmetric about the nose axis, the outer surface defining a first slope at the distal extremity that is coplanar with the nose axis, the first slope defining a first acute angle relative to the nose axis, the mid portion defining a second cross-section that is orthogonal to a nose axis of the nose portion, the outer surface of the nose portion defining a second slope at the mid portion that is coplanar with the first slope, the second slope defining a second acute angle relative to the nose axis,
wherein the first cross-section is smaller than the second cross-section, and the first acute angle is smaller than the second acute angle,
wherein each of the first cross-section and the second cross-section defines a shape that is one of a circular shape and an oblong shape.

* * * * *